US012680063B2

(12) United States Patent
Gray et al.

(10) Patent No.: US 12,680,063 B2
(45) Date of Patent: Jul. 14, 2026

(54) DEVICES AND METHODS FOR THE GENERATION AND EVALUATION OF ENGINEERED TISSUES

(71) Applicant: CURI BIO, INC., Seattle, WA (US)

(72) Inventors: Kevin Gray, Seattle, WA (US); Samir Kharoufeh, Seattle, WA (US); Elliot Fisher, Seattle, WA (US); Jason Silver, Seattle, WA (US); Nicholas Geisse, Seattle, WA (US)

(73) Assignee: CURI BIO, INC., Seattle, WA (US)

( * ) Notice: Subject to any disclaimer, the term of this patent is extended or adjusted under 35 U.S.C. 154(b) by 868 days.

(21) Appl. No.: 17/904,609

(22) PCT Filed: Feb. 25, 2021

(86) PCT No.: PCT/US2021/019748
§ 371 (c)(1),
(2) Date: Aug. 19, 2022

(87) PCT Pub. No.: WO2021/173887
PCT Pub. Date: Sep. 2, 2021

(65) Prior Publication Data
US 2023/0109347 A1     Apr. 6, 2023

Related U.S. Application Data

(60) Provisional application No. 62/981,446, filed on Feb. 25, 2020.

(51) Int. Cl.
*C12M 3/00*     (2006.01)
*C12M 1/00*     (2006.01)
(Continued)

(52) U.S. Cl.
CPC ............ *C12M 21/08* (2013.01); *C12M 23/12* (2013.01); *C12M 23/26* (2013.01); *C12M 35/02* (2013.01)

(58) Field of Classification Search
CPC .............................. C12M 23/12; C12M 21/08
See application file for complete search history.

(56) References Cited

U.S. PATENT DOCUMENTS 7,214,303 B2    5/2007  Naughton
10,732,174 B2   8/2020  Wakatsuki et al.
(Continued)

FOREIGN PATENT DOCUMENTS

CN      207828325 U    9/2018
CN      209508283 U    10/2019
(Continued)

OTHER PUBLICATIONS

International Search Report mailed on Jun. 29, 2021, issued in corresponding International Patent Application No. PCT/US21/19748, filed on Feb. 25, 2021, 4 pages.
(Continued)

*Primary Examiner* — Jonathan M Hurst

(74) *Attorney, Agent, or Firm* — IPkey PLLC

(57)     ABSTRACT

Methods and systems for generating three-dimensional (3D) engineered tissues (ETs), and for electrical stimulation of same, are provided. Provided is an ET assembly comprising an ET lid with first post and second post assemblies coupled
(Continued)

thereto. Provided is a casting assembly comprising the ET assembly and a casting plate. Provided are stimulation methods and systems for stimulating tissue constructs.

20 Claims, 31 Drawing Sheets

(51) Int. Cl.
    *C12M 1/32*        (2006.01)
    *C12M 1/42*        (2006.01)

(56) References Cited

U.S. PATENT DOCUMENTS

| | | |
|---|---|---|
| 12,384,999 B2 | 8/2025 | Dendorfer |
| 2008/0105607 A1 | 5/2008 | Shigesada et al. |
| 2013/0029412 A1 | 1/2013 | Reis et al. |
| 2013/0109012 A1 | 5/2013 | Sniadecki et al. |
| 2013/0181323 A9 | 7/2013 | Lin |
| 2015/0056643 A1 | 2/2015 | Sniadecki et al. |
| 2016/0030177 A1* | 2/2016 | Eschenhagen ....... A61B 5/1108 73/866.4 |
| 2017/0260488 A1 | 9/2017 | Costa et al. |
| 2019/0029549 A1 | 1/2019 | Sniadecki et al. |
| 2019/0083974 A1* | 3/2019 | Cambron .............. B01L 3/5025 |
| 2019/0186921 A1 | 6/2019 | Klosinski, Jr. et al. |
| 2020/0255789 A1 | 8/2020 | Dendorfer |
| 2020/0305765 A1 | 10/2020 | Herr et al. |
| 2021/0270922 A1 | 9/2021 | Martens et al. |

FOREIGN PATENT DOCUMENTS

| | | |
|---|---|---|
| DE | 102010052197 A1 | 5/2012 |
| WO | 2014210388 A1 | 12/2014 |
| WO | 2017093529 A1 | 6/2017 |
| WO | 2019/008505 A1 | 1/2019 |
| WO | 2019060370 A1 | 3/2019 |
| WO | 2019106438 A1 | 6/2019 |
| WO | 2021071954 A1 | 4/2021 |
| WO | 2022015869 A1 | 1/2022 |

OTHER PUBLICATIONS

Written Opinion of the International Searching Authority mailed on Jun. 29, 2021, issued in corresponding International Patent Application No. PCT/US21/19748, filed on Feb. 25, 2021, 7 pages.

Hansen, A. et al., "Development of a Drug Screening Platform Based on Engineered Heart Tissue" Circulation Research: New Methods in Cardiovascular Biology; Jul. 9, 2010, pp. 35-44.

Japanese Notice of Reasons for Refusal mailed on Feb. 19, 2024, issued in the corresponding Japanese App. No. 2022-551564 filed on Aug. 24, 2022, and its English translation thereof; 10 pages.

Supplementary European Search Report mailed on Mar. 1, 2024, issued in the corresponding European App. No. 21761402.3 filed on Aug. 11, 2022; 7 pages.

* cited by examiner

112b

112a

800

802a

803

803

803

803

1

DEVICES AND METHODS FOR THE GENERATION AND EVALUATION OF ENGINEERED TISSUES

CROSS-REFERENCE TO RELATED APPLICATIONS

This application is a National Stage of International Application No. PCT/US2021/019748, filed Feb. 25, 2021, which claims priority to U.S. Provisional Patent Application No. 62/981,446, filed Feb. 25, 2020, the entire disclosures of which are hereby incorporated by reference.

BACKGROUND

Technical Field

The present application is directed to methods and systems for generating three-dimensional (3D) engineered tissues (ETs), and methods and systems for electrical stimulation and measurement of contractility and various physiological characteristics of same.

Description of the Related Art

Three-dimensional engineered tissues (referred here as ETs), or tissues thicker than one-cell layer that are manufactured or augmented by an artificial process, are of considerable interest in biomedical research for their cost, availability, and remarkable ability to mimic human physiological tissues, when compared with competing physiological models. Means fabricating, maintaining, and characterizing these ETs have accumulated much academic interest. A particularly sought-after ET system is referred to as a 2 post system, where a tissue is cast between two posts, at least one of which is flexible enough to bend under the contractions of the tissue to which it is adhered. The bending of the post can be related to the force the tissue generates, which can provide meaningful information regarding the health and function of the tissue. Attempts to commercialize this sort of device exist, but the methods resemble more something native to an academic lab than an efficient, industry-focused tool.

U.S. Publication No. 2019/0029549 by Sniadecki et al. discloses such a two-post ET system. A magnet embedded into one post of the two-post ET system of Sniadecki provides magnetic sensor-based detection of contractile forces of ETs residing in a multiwell plate. This non-optical contractile assay system enables the measurement of a force exerted by a 3D ET suspended between a magnet-embedded flexible post and a rigid post, and uses a magnetometer to detect a change in the magnetic field resulting from a deflection of the flexible post as the ET undergoes contractile actions. Other commercially available 2 post systems provide optical readouts of post bending under ET load, as described in Hensen et al. The publication Development of a Drug Screening Platform Based on Engineered Heart Tissue, Circulation Research; Jul. 9, 2010 downloadable from http://circres.ahajournals.org.

Previously disclosed ET systems, however, have limitations terms of manufacturing throughput, ease of use, and ergonomics. Fabrication of non-biological components of the system require complicated molding and demolding processes that could take several days. Such fabrication processes are often times non compatible with industry standard fabrication techniques such as compression or injection molding, or require unconventional modifications to said techniques to achieve scalability.

The process for generating the 3D tissues themselves is a significantly limiting factor. In many 2 post systems, ETs are cast from a suspension of cells and extracellular matrix that gels around the posts after being deposited in a mold. The operator is required to cast the mold for the tissues themselves within the wells of a tissue culture plate out of a highly temperature-sensitive gel material, such as gelatin or agarose, which detrimentally affects reproducibility and throughput of the 3D tissue constructs. Other materials such as silicone can be used, but require laborious surface treatments to render the molds nonadherent to tissues. The handles on which theses posts that hold the tissues are mounted have no alignment features that ensure their consistent placement within the trenches, leading to highly variability in the morphologies of cast tissues. Additionally, once cast, these gel molds have trenches with vertical walls that make removal of the tissue constructs difficult due to friction between the tissue constructs and the sides of the mold.

Newly-formed tissues are delicate and any slight adherence to the casting substrate can cause catastrophic failure of the tissue cast. The components on which the two posts are mounted lack features for efficiently and reproducibly interfacing with industry standard culture devices and have limited ability to integrate into automated handling systems due to their unwieldly shapes. They may be easily and deleteriously misaligned with any sensors intended to evaluate the tissue. Slight misplacement of the device on a microplate may squish the tissue between the top surface of the microplate and the substrate on which the posts are mounted. They cannot be readily handled in groups of more than 6 at a time, and lack features by which a human or robotic operator can grip easily.

The performance of ETs can be enhanced in many ways by electrical stimulation, while of great interest, this also presents challenges. Conventional electrical stimulation devices used in cell culture typically involve graphite rods or platinum wires permanently affixed to an electrical stimulation module that fits over the top of a microplate with the electrodes protruding into the media bath of each well in the microplate. As small molecules in the media bath permeate and attach to graphite electrodes easily, the graphite electrode assembly needs to be replaced after only a single drug-screening experiment to avoid cross-contamination. However, available such graphite stimulation devices are either too costly as a single-use consumable, or quite challenging to assemble and integrate into industry standard tissue cultureware, limiting the commercial utility of such devices in high-throughput stimulation studies. While platinum electrodes lack the porosity of graphite electrodes, giving them an edge in terms of reusability, they have a higher propensity to generate cytotoxic electrolytic bi-products and require extensive cleaning after use, which negatively impacts their utility in high-throughput biological studies. Platinum wire is also quite expensive, limiting the commercial scalability of devices that employ it. Additionally, no two post system incorporates means of stimulating and recording from tissues using the posts themselves as electrodes. Since electrophysiology is another important metric of tissue function, and can be combined with contractile behavior to give a highly informative view the state of a given ET, incorporation of recording functionality would be of great benefit. Stimulation of the tissue using the posts can also reduce the voltage required to stimulate the tissue due to the tissue's proximity to the electrode surface.

This reduces the potential for toxic byproduct formation that would be incurred by other more remote stimulation delivery methods.

BRIEF SUMMARY

The present application is directed to methods and systems for generating three-dimensional (3D) engineered tissues (ETs), such as engineered heart tissues (EHT), engineered skeletal muscle tissues (EMT) and other types of engineered tissues of excitable or contractile cells, and methods and systems for electrical stimulation and measurement of contractility and various physiological characteristics of same. Provided is an ET assembly comprising an ET lid with pairs of post assemblies coupled thereto. Provided is a casting assembly comprising the ET assembly and a casting plate. Provided are stimulation lids and plates.

One embodiment is directed to an engineered tissue (ET) assembly comprising an ET mounting lid, at least one flexible post assembly and an optional rigid post assembly. The ET mounting lid comprises a plate comprising a first side, a second side, a plurality of through holes. The at least one rigid post assembly comprises a first body comprising a plurality of rigid posts. The at least one flexible post assembly comprising a second body comprising a plurality of flexible posts. The plurality of rigid posts and flexible posts are arranged in pairs of posts comprising a rigid post and a flexible post. The pairs of posts are received in respective through holes of the ET mounting lid or are at sides of the through holes.

In another embodiment, the ET assembly may be coupled to a casting plate comprising a plurality of casting wells. The pairs of posts are received in respective through holes of the ET mounting lid and respective casting wells of the plurality of casting wells of the casting plate.

In another embodiment a stimulation plate for stimulating tissue constructs is provided. The stimulation plate comprises a body comprising a plurality of bottomless wells having an upper surface and a lower surface. The bottomless wells of the body are configured to receive the tissue constructs at the upper surface. The stimulation plate further includes a backing plate coupled to the lower surface of the body. The backing plate comprising pairs of electrodes, each pair of electrodes corresponding with a well of the plurality of bottomless wells and configured to electrically communicate with the tissue constructs in the respective bottomless wells.

Another embodiment is directed to a stimulation lid comprising first and second substrates. The first substrate comprising a plurality of holes arranged in pairs. The second substrate is coupled to the first substrate and comprises a plurality of sockets, each socket including two pogo pins. The stimulation lid further includes a plurality of electrode rods arranged in pairs. Each rod of the plurality of rods extending through respective holes of the plurality of holes of the first substrate. The pairs of rods are removably coupled to the two pogo pins of each socket. The first substrate is configured to couple to a surface of a casting plate comprising a plurality of wells having tissue constructs such that distal ends of pairs of the electrode rods are configured to extend into respective casting wells of a tissue culture microplate.

DETAILED DESCRIPTION

Figure 1A:
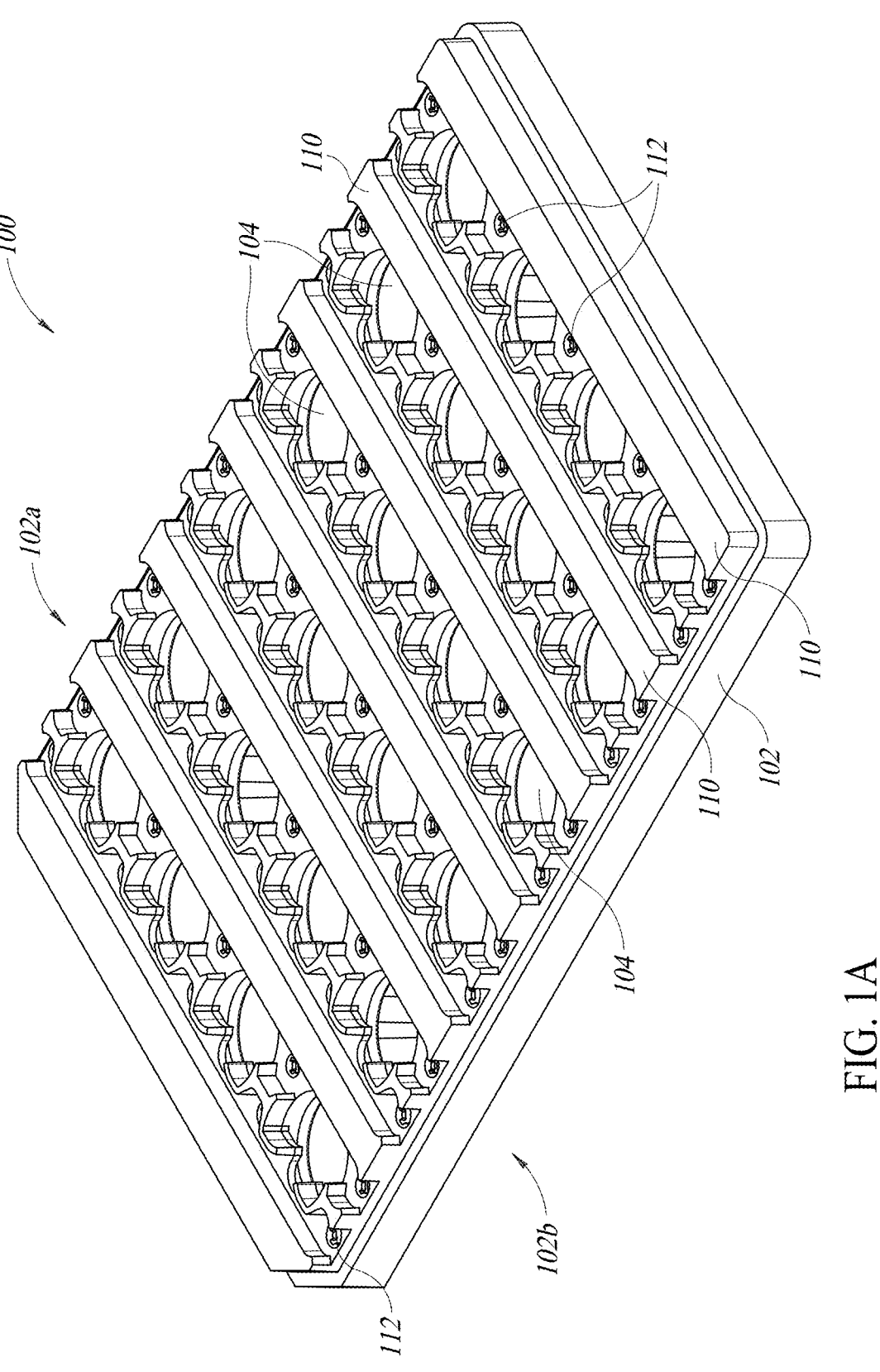
FIG. 1A-1D show various views of an engineered muscle tissue (ET) mounting lid in accordance with one embodiment.
Figure 1B:
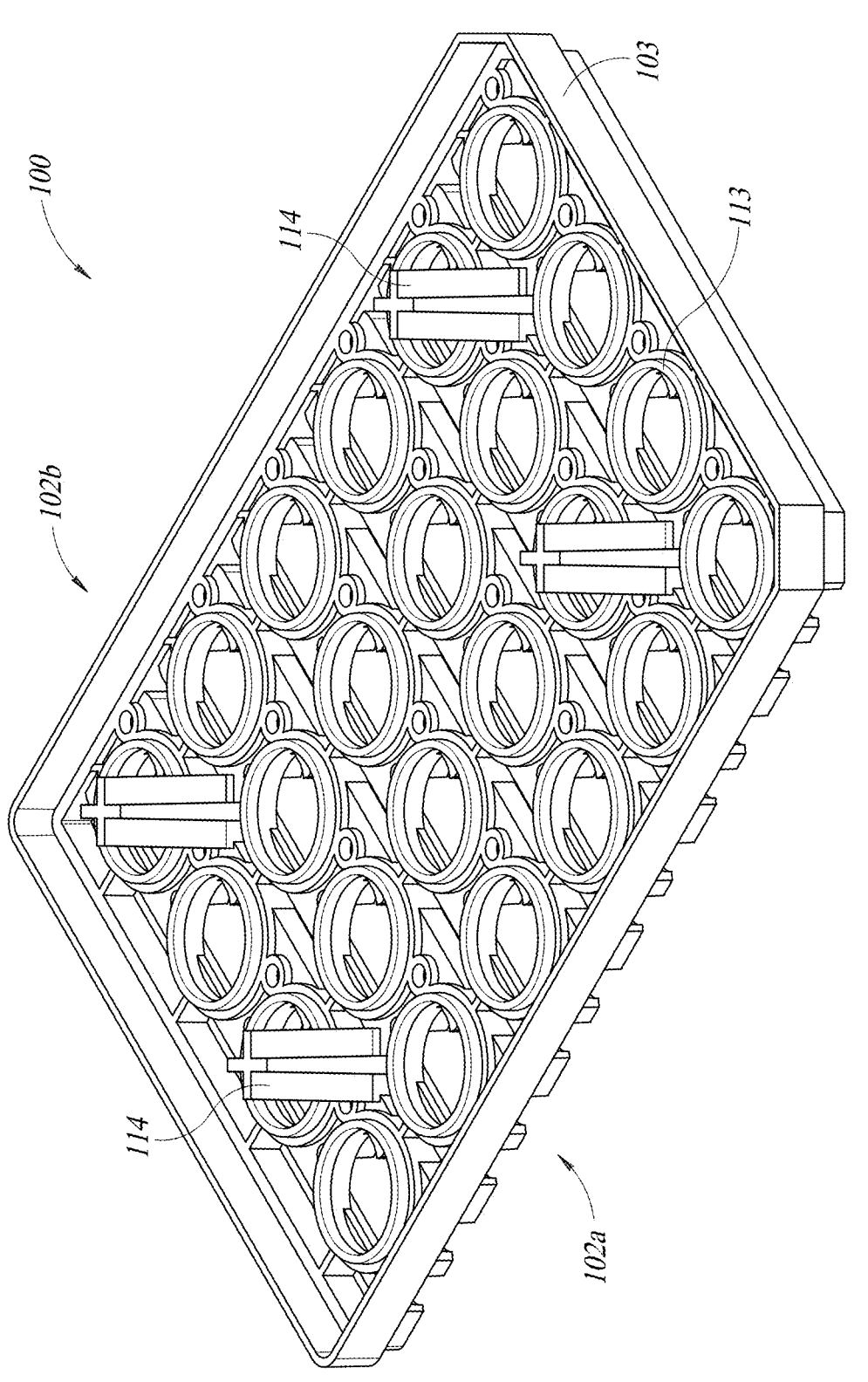
Figure 1C:
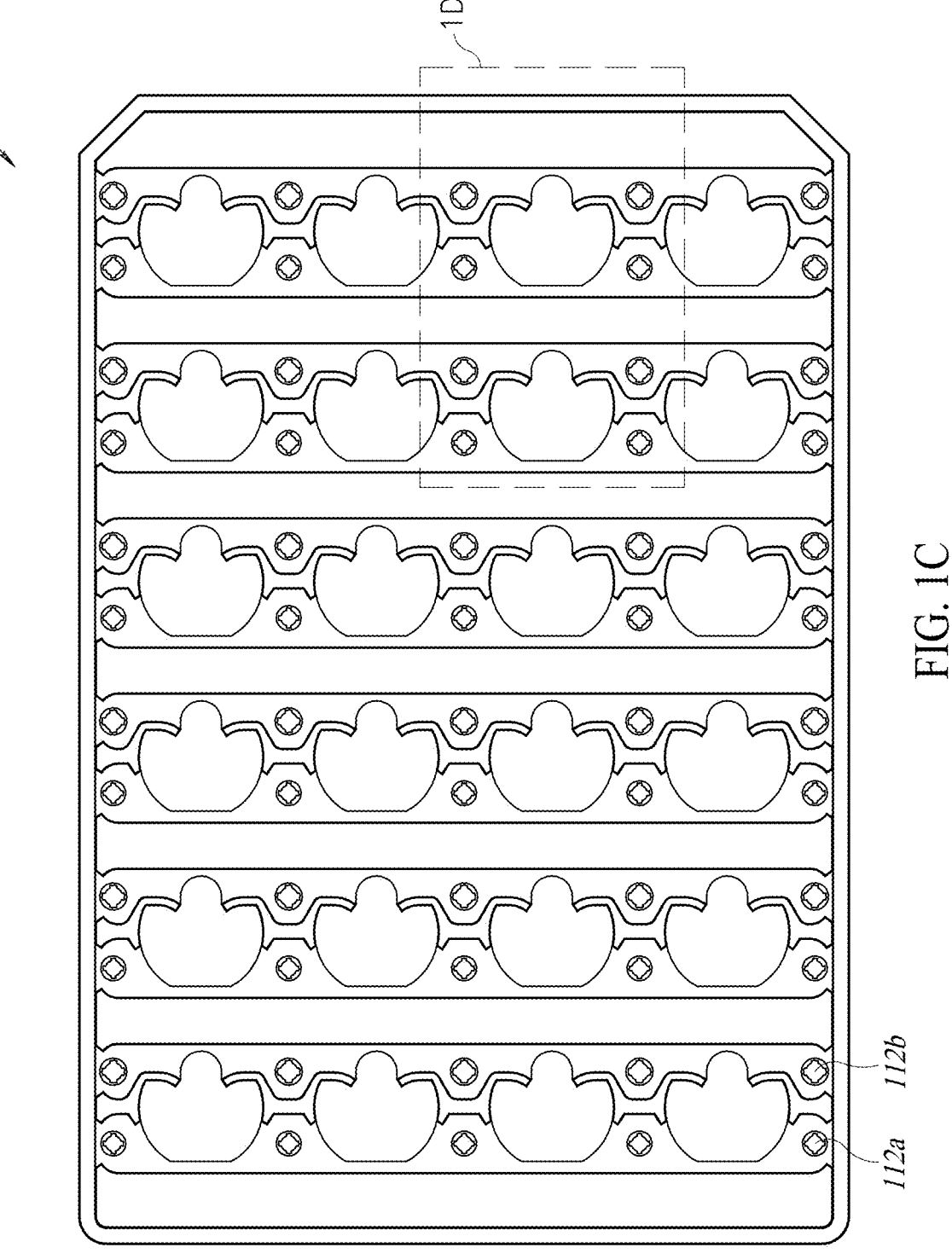
Figure 1D:
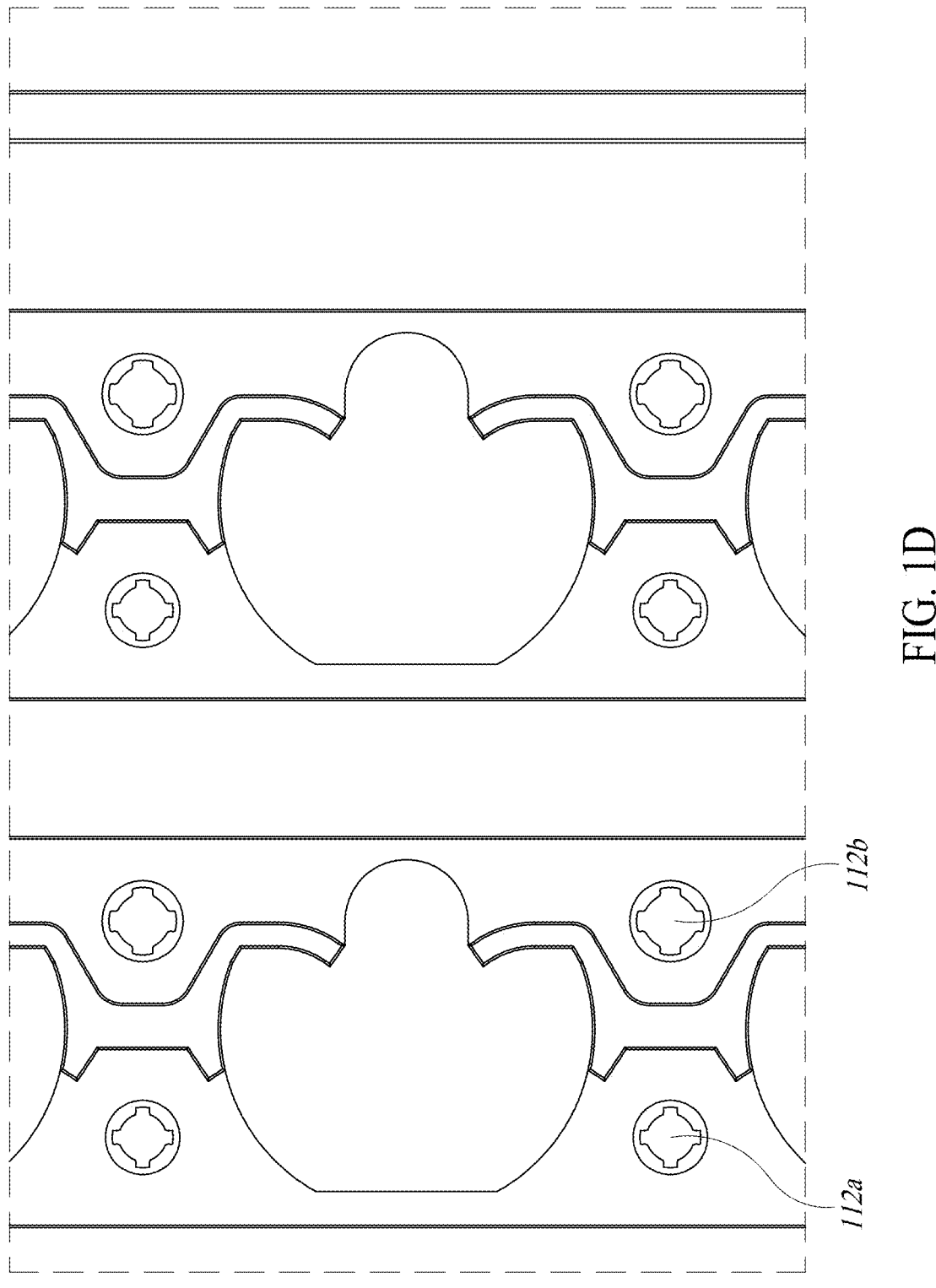

FIG. 1A is a top isometric view of an ET mounting lid in accordance with one embodiment. FIG. 1B is a bottom isometric view of the ET mounting lid of FIG. 1A. FIG. 1C is a top plan view of the ET mounting lid of FIG. 1A. FIG. 1D is an exploded top plan view of a portion of the ET mounting lid as shown in FIG. 1C. The ET mounting lid is configured to be used in combination with a casting plate (or microplate) for growing engineered tissue.

The ET mounting lid 100 comprises a lattice structure formed from one or more rigid plates 102. Around rigid plates 102 extends a skirt 103 from second side 102b that provides a region for a human or robotic operator to grasp EMT mounting lid 100, as well as providing a region for placement of a barcode or other information important for identification of a specific device. The ET mounting lid 100 includes an array of through openings 104 extending from a first side 102a of the plate 102 to a second side 102b of the plate 102. The array of the through openings 104 in FIGS. 1A-1C shows an array of four columns by six rows, however, any array size may be used and an arrangement other than an array may be used.

The size and shape of each through opening 104 may be different at the first and second sides 102a, 102b of the ET mounting lid 100. In one embodiment, the walls at the through openings 104 slope at an angle between the first and second sides 102*a*, 102*b*. In another embodiment, the walls at the through openings 104 extend perpendicularly between the first and second sides 102*a*, 102*b*.

The through openings 104 are configured to overlap with wells of a microplate, such as the casting plate of FIG. 4A as will be explained below. Thus, the arrangement of the through openings 104 of the ET mounting lid 100 corresponds to the arrangement of casting wells of the casting plate such that at least portions of the through openings 104 overlap with portions of the casting wells of the casting plate. The size and shape of the through openings 104 of the ET mounting lid may be of any shape or size that allow posts to extend into the casting wells of the casting plate as will be explained below.

The ET mounting lid 100 includes coupling members 112 at opposing sides of each row. The coupling members 112 of the ET mounting-100 are located outwardly of the through openings 104. The coupling members 112 are configured to et gage with coupling elements of post assemblies of FIGS. 2A and/or 2B as will be explained below. In one embodiment and with reference to FIGS. 1C and 1D, coupling members 112*a* may be of a different size and/or shape of coupling members 112*b*. In the illustrated embodiment, the rows of coupling members 112 are receiving members, such as slots or openings, configured to receive a coupling element, such as a pin, of the post assembly. In another embodiment, the rows of 112 are pins, while the post assembly has the receiving members.

The ET mounting lid 100 includes a plurality of rigid strips 110 extending between each row of through openings 104 and at opposing ends of the ET mounting lid 100. The flat rigid strips 110 provide stiffness to the ET mounting lid 100 and help align and secure various components affixed to ET mounting lid 100 and protect against perturbations due to handling. In the illustrated embodiment, each row includes four through openings 104 separated by respective rigid strips 110. The rigid strips 110 are located at the first side 102*a* of the ET mounting lid 100, however, the rigid strips 110 may be located at a second side 102*b*. The rigid strips 110 are integrally formed in a single rigid plate 102; however, in other embodiments, the rigid strips 110 may be separable components couple to a surface of the plate 102.

With reference to FIG. 1B, the through openings 104 at the second side 102*b* of the ET mounting lid 100 include protruding rings 113 that extend away from the second side of the ET mounting lid 100. The protruding rings 113 provide an alignment feature for when coupling the ET mounting lid 100 to multiwell tissue culture plates, including a casting plate, as will be discussed in more detail in reference to FIGS. 5A-5C.

The second side 102*b* of the ET mounting lid 100 includes a plurality of pegs 114 extending orthogonally from the second side 102*b*. The pegs 114 are rigid and configured to mate with receiving portions of the ET mounting lid 100 with a casting late to removably secure the ET mounting lid to the casting plate as will be explained in more detail below with reference to FIGS. 5A-5C. Accordingly, the size and shape of pegs 114 correspond to receiving portions, gaps, of the casting plate. Although four pegs 114 are shown, the second side of the ET mounting lid 100 may have any number of pegs, including more or fewer pegs.

The ET mounting lid 100 may be made from one or more molded, milled, or 3D printed, with injection molding being the preferred process parts. The molding material may be rigid thermoplastics, and in some embodiments one or more parts may be made from elastomeric thermoset or thermoplastic.

Figure 2A:
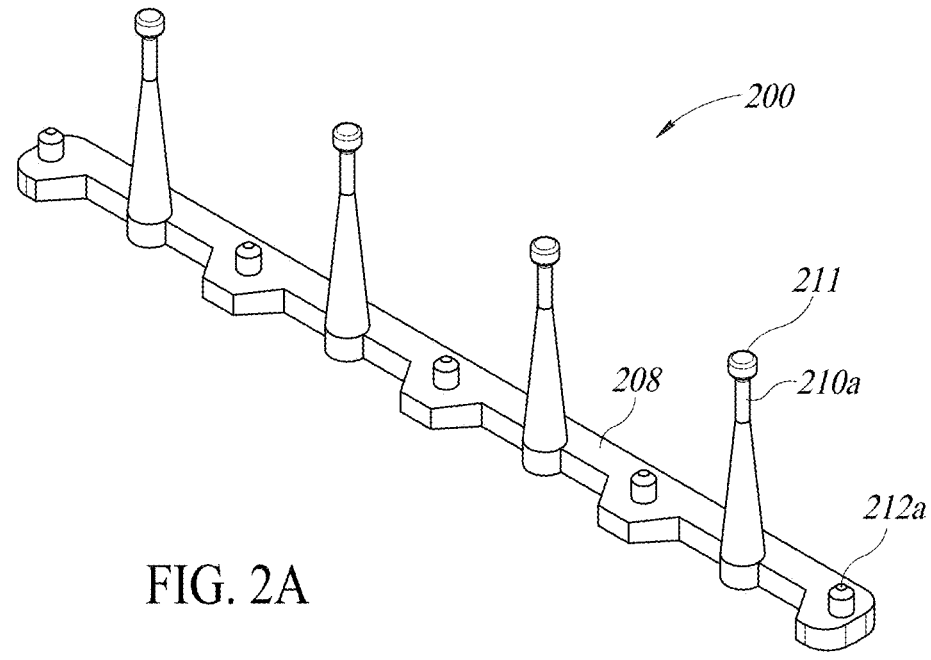
FIG. 2A is a top isometric view of rigid post assembly in accordance with one embodiment.
Figure 2B:
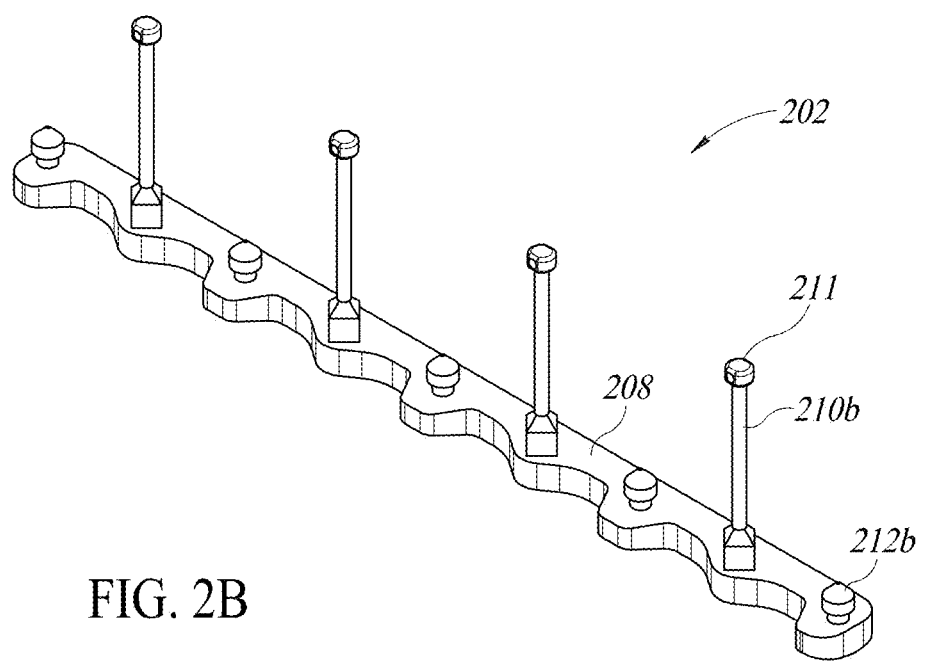
FIG. 2B is a top isometric view of a flexible post assembly in accordance with one embodiment.
Figure 2C:
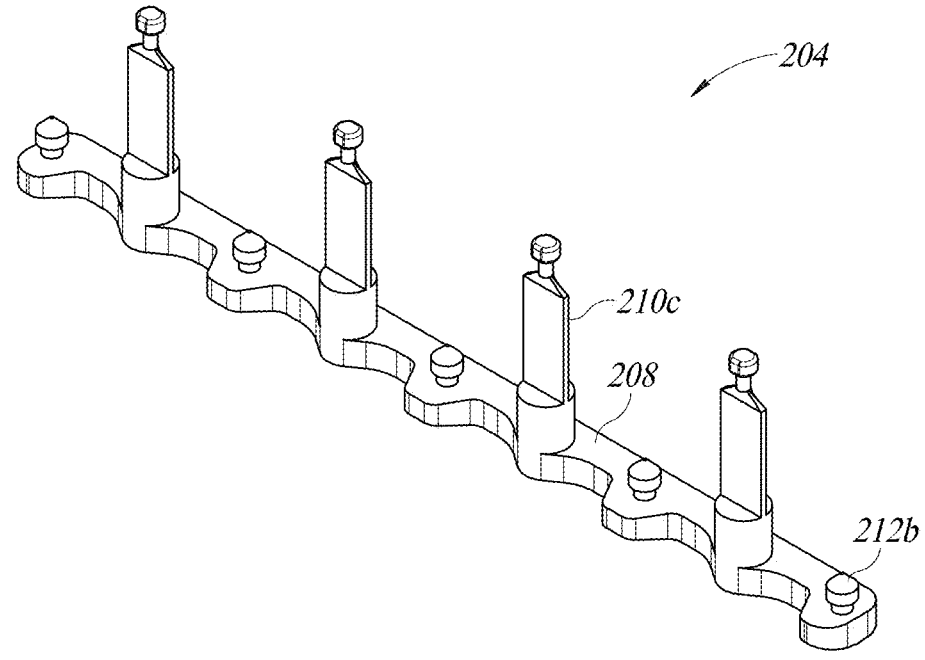
FIG. 2C is a top isometric view of a flexible post assembly in accordance with another embodiment.

The through openings 104 at the first side 102*a* of the ET mounting lid 100 are configured to receive a plurality of post assemblies, such as the post assemblies of FIGS. 2A, 2B, and 2C.

FIG. 2A shows a rigid post assembly 200, while FIGS. 2B and 2C show alternative flexible post assemblies 202, 204. Both the rigid and the flexible post assemblies 200, 202, 204 comprise a base 208, a plurality of posts 210*a*, 210*b*, 210*c* extending from the base 208, and a plurality of coupling elements 212*a*, 212*b*, which in the illustrated embodiments are pins. Each row of the ET mounting lid 100 is configured to receive the rigid post assembly 200 of FIG. 2A at a first side of the row proximate a first rigid strip 110 and the flexible post of assembly of FIG. 2B (or FIG. 2C) at a second side of the row proximate another rigid strip 110.

Proximal ends of the posts 210*a*, 210*b*, 210*c* are coupled to the base 208 and distal ends of the posts 210*a*, 210*b*, 210*c* extend away from the base 208. The respective plurality of posts 210*a*, 210*b*, 210*c* and base 208 form a single monolithic component, which may be formed from elastomeric material. The base 208 has dimensions to provide suitable rigidity for supporting the posts 210*a*, 210*b*, 210*c*; however, the base 208 may be flexible. The distal ends 211 of the posts may incorporate additional anchoring features to securely couple any over-molded material, such as tissue, to the posts.

Generally described, the posts 210*a*, 210*b*, 210*c* are conventional posts, made from a polymeric material, configured to allow tissue to grow therebetween. The number and positions of posts 210*a*, 210*b*, 210*c* extending from each base 208 correspond to the number and position of through openings 104 in the ET mounting lid 100. More particularly, the plurality of posts 210*a*, 210*b*, 210*c* are spaced apart from each other in a manner that corresponds to the through openings 104 of the ET mounting lid 100 such that when the post assemblies 200, 202, 204 are installed on the ET mounting lid 100, the posts 210*a*, 210*b*, 210*c* extend into through openings 104 of the ET mounting lid 100 as best shown in FIG. 3E.

Between adjacent posts 210*a*, 210*b*, 210*c* of the post assemblies 200, 202, 204 are coupling elements, which are pins 212*a*, 212*b* extending from the base 208. The pins 212*a*, 212*b*, are configured to mechanically couple the post assemblies 200, 202, 204 to the ET mounting lid 100. In particular, the pins 212*a*, 212*b* are arranged and dimensioned to be inserted into respective slots of each row at the first side of the ET mounting lid 100 to thereby secure the post assembly to the ET mounting lid 100. The pins 212*a* of the rigid post assembly 200 may be different from the pins 212*b* of the flexible post assemblies 202, 204 to aid the assembler. Accordingly, the coupling members 112*a* of the ET mounting lid 100 may be of a first size, as shown in FIG. 1D, for receiving the rigid post assembly 200, while the coupling members 112*b* of the ET mounting lid 100 is of a second, different size.

The pins 212*a*, 212*b* may include a locking feature, such as a lip, that presses against the second side 102*b* of the ET mounting lid 100 to aid in securing post assemblies 200, 202, 204 to the ET mounting lid 100. The above described coupling mechanism between the ET mounting lid 100 and the post assemblies 200, 202, 204 are male and female components. Although the ET mounting lid 100 is shown as having the female component and the post assemblies 200, 202, 204 are shown as having the male component, it is to be appreciated that the ET mounting lid 100 can have the male component and the post assemblies 200, 202, 204 can have the female component. Furthermore, any other mechanical coupling between the ET mounting lid and the post assemblies may be used.

The difference between the flexible post assemblies 202, 204 and the rigid post assembly 200 is that the flexible post assemblies 202, 204 include a plurality of flexible posts 210b, 210c that are flexible to forces associated with tissue constructs and electrical stimulation of same, while the rigid post assembly 200 includes a plurality of rigid posts 210a, which are rigid to the forces associated with tissue constructs and the electrical stimulation of same.

The flexible posts 210b of FIG. 2B have a greater diameter (or dimension) at their proximal end and a smaller diameter along the majority of their lengths. This allows the post bending stiffness to be tuned to the given application without changing the geometry of the distal end. The flexible posts 210b may be configured to flex in all planes, including perpendicular planes. The flexible posts 210c of FIG. 2C have a flat, rectangular shape along a majority of its length from the proximal end and tapers to a narrower region towards their distal end. The flexible posts 210c of FIG. 2C are configured to flex in a single plane in response to one or more forces associated with growing tissue constructs and electrical stimulation of same, while remaining rigid in transverse planes.

The rigid posts 210a are orders of magnitude stiffer than the flexible posts 210b, 210c as is well known in the art. The rigid posts 210a are made of suitable shapes and material such that they remain rigid when exposed to tissue forces, such as forcer during tissue growth and testing, while the flexible posts 210b, 210c are made of suitable shapes and materials such that they flex in at least one or more directions when exposed to the tissue forces. For example, the rigid posts 210a may be made of rigid thermoplastics such as, but not limited to polystyrene or polycarbonate.

The flexible posts 210b, 210c may include a magnet at the distal end 211. The magnet may be embedded inside the elastomeric material or coupled to the outer surface. The flexible posts 210b, 210c may be made of an elastomeric material. Both the rigid posts and the flexible posts may include a cap at the distal end to securely couple any over-molded biological tissue to the post. The flexible posts act as a transducer for the force generated by this tissue; by knowing the mechanical properties of the post, as well as the post bends loaded by the tissue, one can estimate the force the tissue is generating at any given time, which can yield meaningful information about the health and function of the tissue.

U.S. Publication No. 2019/0029549 by Sniadecki describes further details of rigid and flexible posts and tissue growth and is incorporated herein in its entirety for all purposes. While this patent also discloses device using a rigid/flexible post pair, the rigid post described herein can achieve higher rigidity than in that disclosure due to being made of high rigidity thermoplastic and mounted to a high rigidity thermoplastic. While the aforementioned disclosure utilizes a rigid insert embedded into an otherwise flexible post, protruding from a base of flexible material, such that the post can still displace under loads sometimes generated by ETs due to flexure of the unsupported elastomeric base from which it protrudes. The rigid post assemblies 200 in our device are securely fixtured to the rigid ET mounting lid 100 such that they will not displace due to ET contraction.

In one embodiment, pairs of posts comprising one rigid post and one flexible post are configured to hold an ET construct therebetween, using various cell culture and tissue generation techniques that are generally known in the art. In other embodiments, the pairs of posts comprise two flexible posts configured to hold an ET construct therebetween.

Figure 3A:
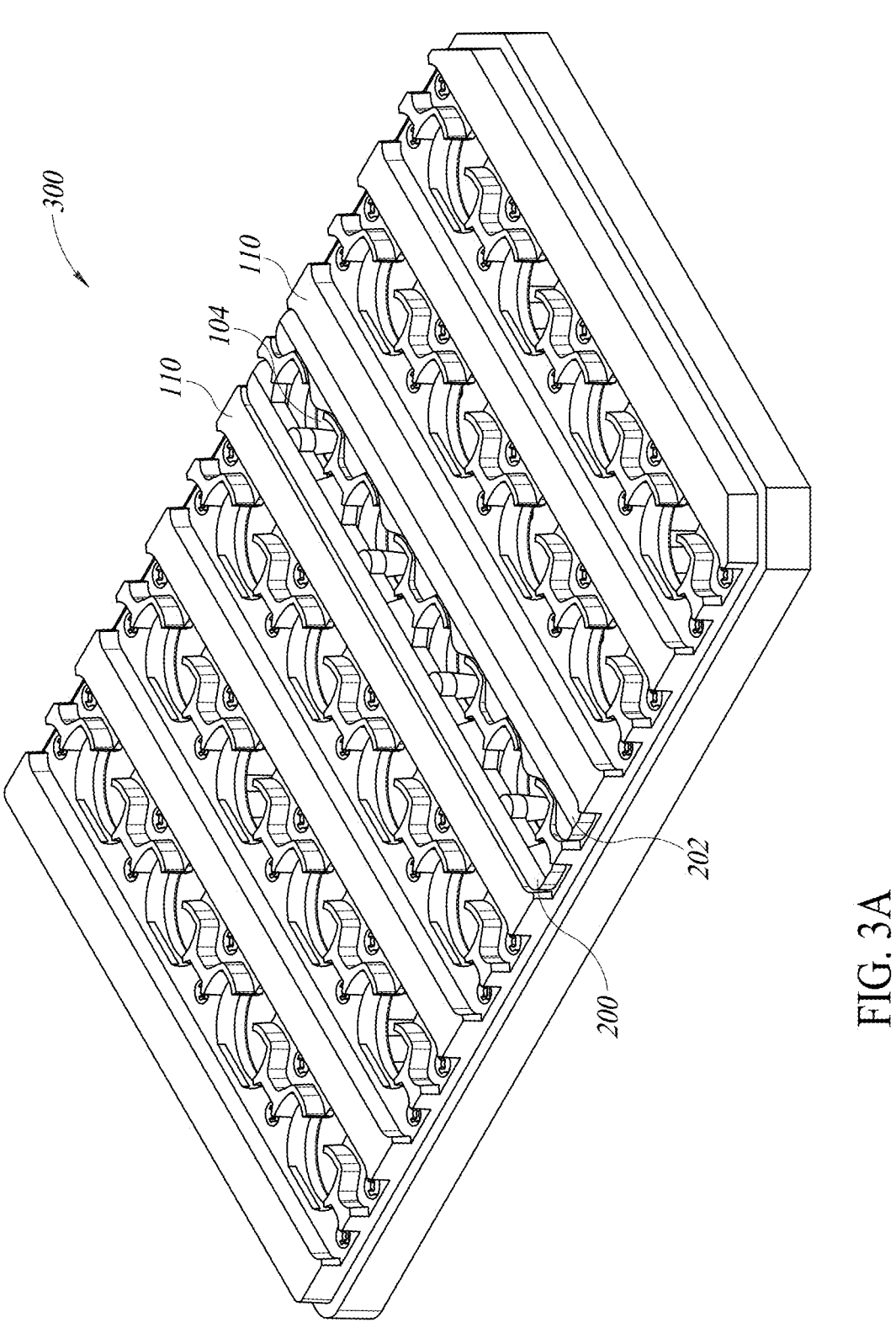
FIG. 3A-3E show various views of a partially assembled ET assembly in accordance with one embodiment.

FIG. 3A is a top isometric view of a partially assembled ET assembly 300 that includes the ET mounting lid 100 of FIG. 1A and the post assemblies 200 and 202 in accordance with one embodiment. Only a single pair of rigid post assembly 200 and flexible post assembly 202 is coupled at a single row of the first side 102a of the ET mounting lid 100 for simplicity and ease of explanation.

Figure 3B:
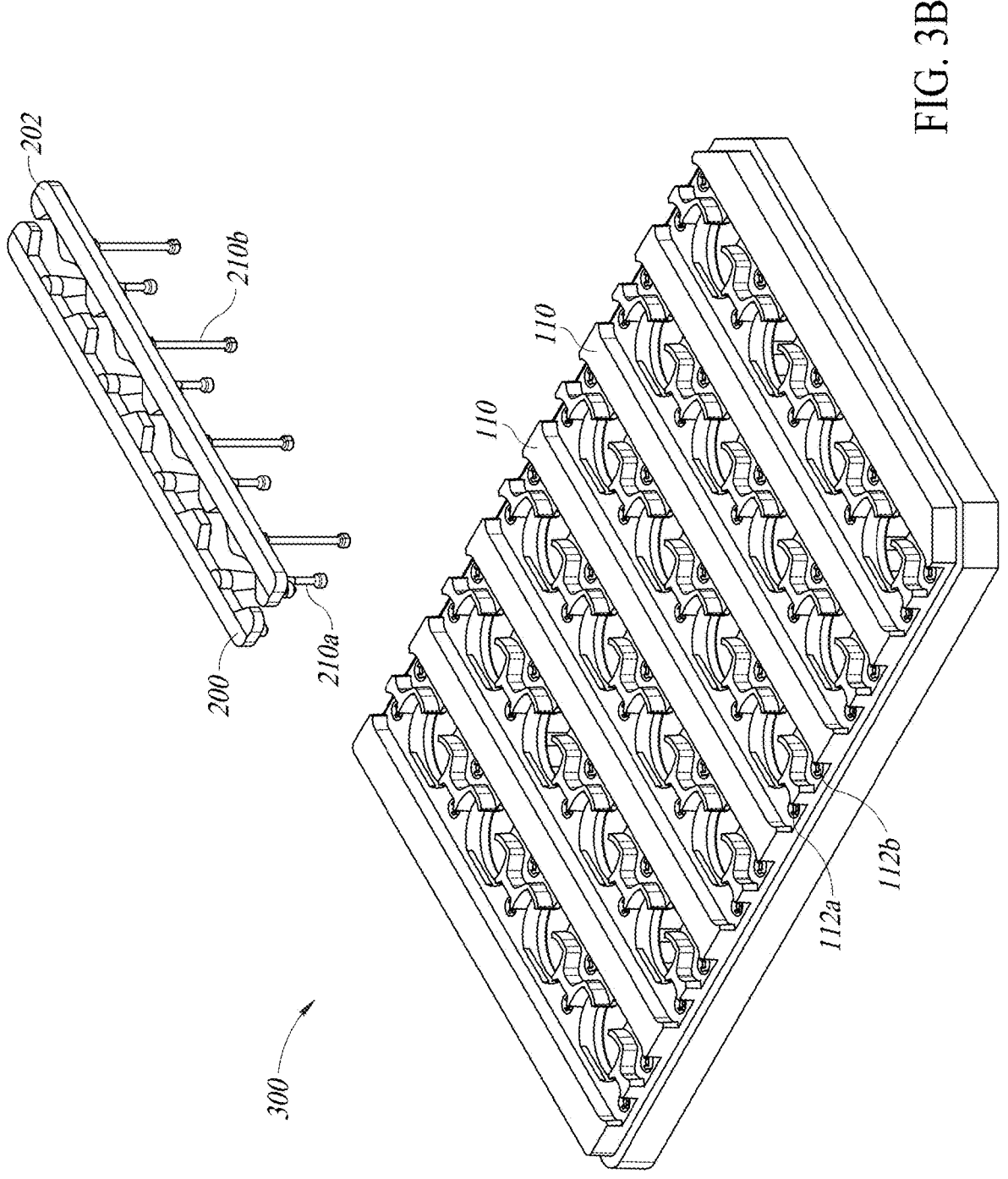
Figure 3C:
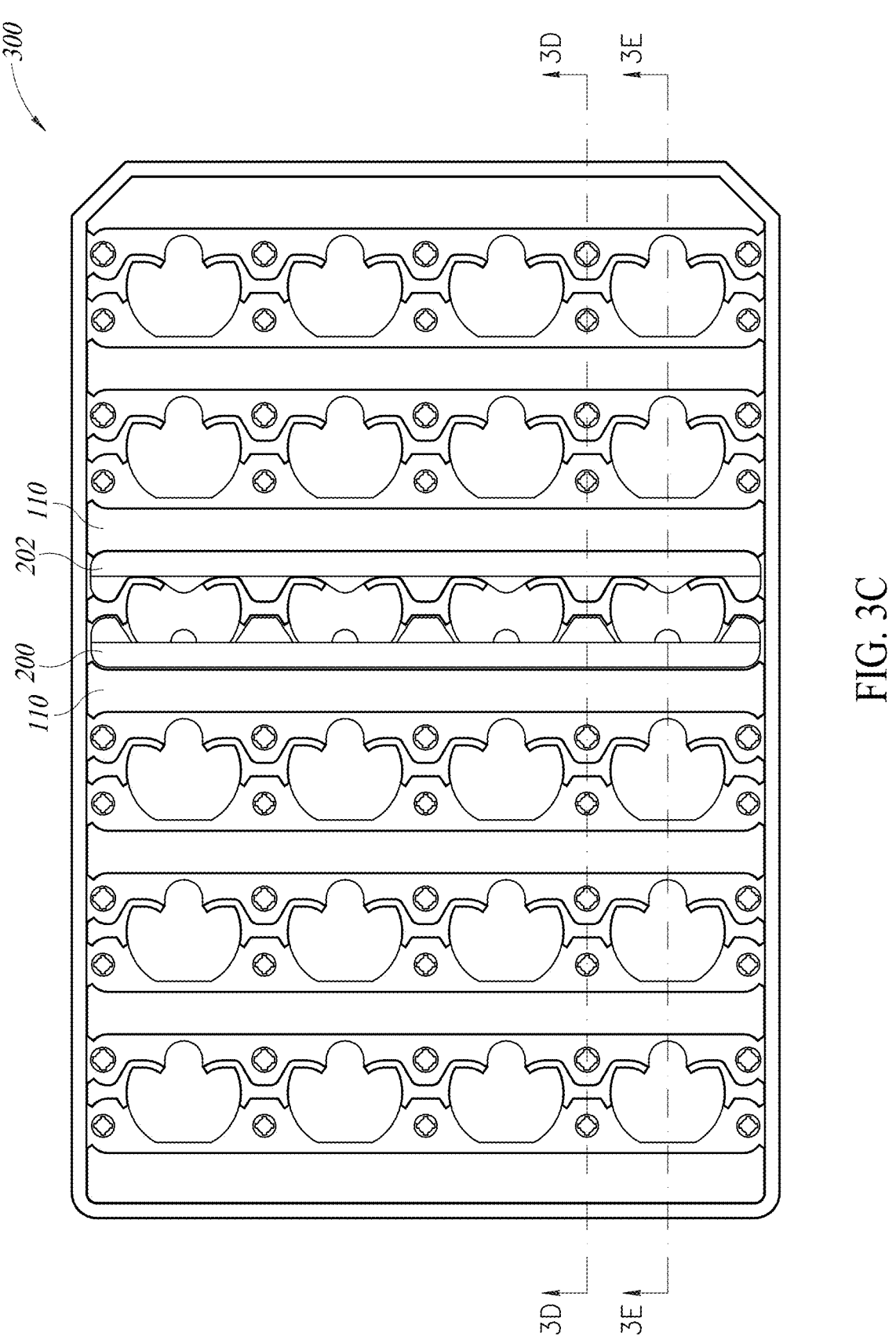
Figures 3D, 3E:
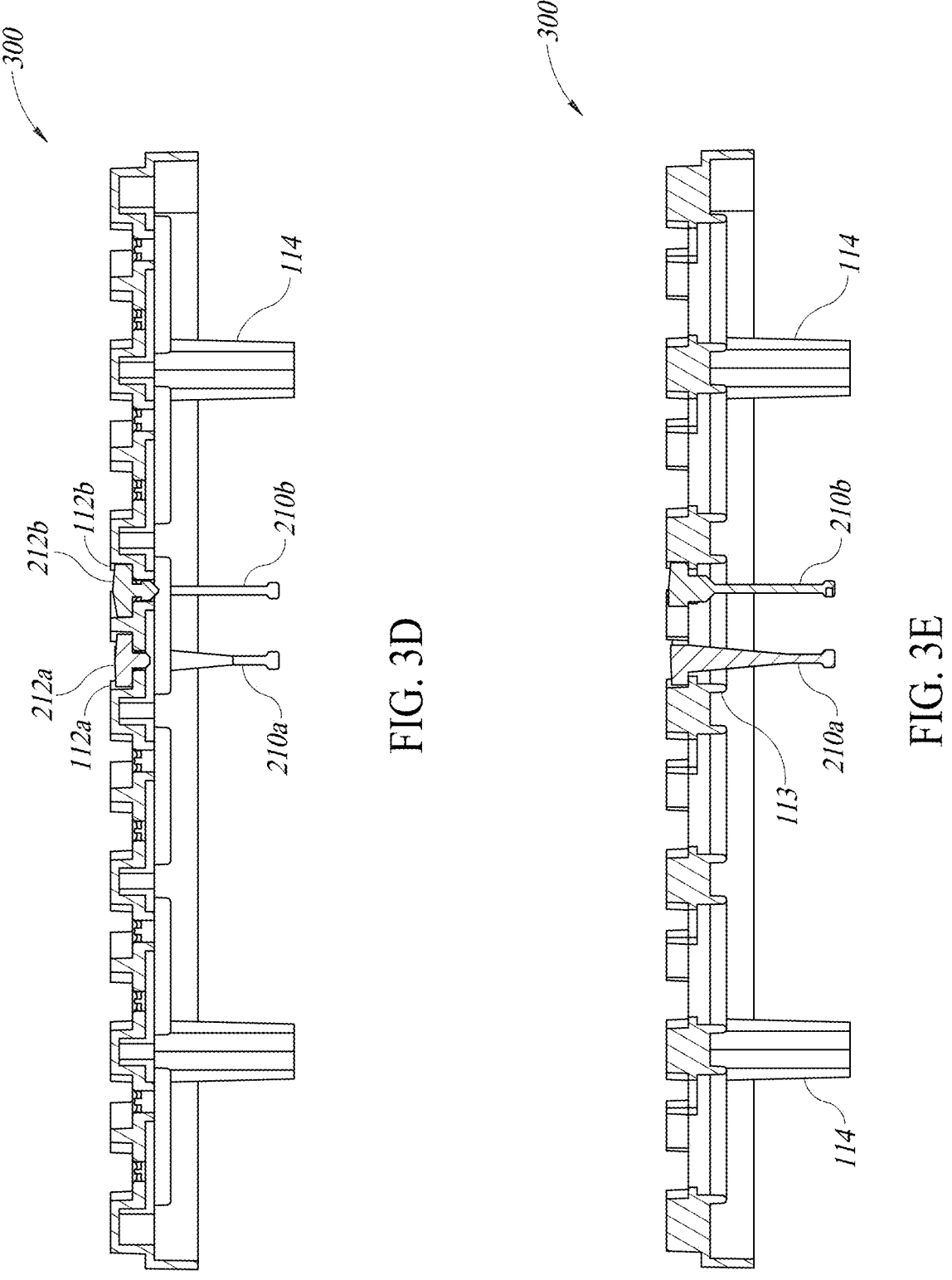

FIG. 3B shows the partially assembled ET assembly 300 of FIG. 3A in exploded view such that the pair of rigid post assembly 200 and flexible post assembly 202 are not coupled to the ET mounting lid 100. FIG. 3C is a top view of the partially assembled ET assembly 300 of FIG. 3A. FIG. 3C showing cross section line locations of the cross sectional views shown in FIGS. 3D and 3E. Although only a single rigid post assembly and a single flexible post assembly are installed in a single row of the ET mounting lid, all of the rows will have a respective rigid and flexible post assembly installed to form a fully assembled ET assembly as shown in FIG. 3F.

As best shown in FIG. 3D, the coupling members 112a of the ET mounting lid 100 receive the pins 212a, 212b of the post assemblies 200, 202 to secure the post assemblies to the ET mounting lid by press fit configuration. Pairs of posts, each pair comprising one rigid post 210a and one flexible post 210b, extend into respective through openings at opposing sides of the through openings as best shown in FIG. 3E. The rigid post assembly 200 and the flexible post assembly 202, when installed in the ET mounting lid 100, are separated from each other by a gap as best shown in FIG. 3A. The pairs of posts 210a, 10b, when installed in the ET mounting lid 100 to form the ET assembly, are a particular distance from each other with respect to their center axes, which in some embodiments may be between 4 mm and 20 mm, as is conventional in the art to allow tissue constructs to grow therebetween.

As shown in FIGS. 3D and 3E, the pegs 114 of the ET mounting lid 100 are longer than the rigid and flexible posts 210a, 210b. That is, distal ends of the pegs 114 are farther from the second side 102b of the ET mounting lid 100 than the distal ends of the flexible and rigid posts 210a, 210b. Each peg 114 acts as an alignment guide for coupling the ET assembly 300 with a casting plate as will be explained below in reference to FIG. 5A-5C. In particular, the pegs 114 are received in receiving members of the casting plate.

Figure 3F:
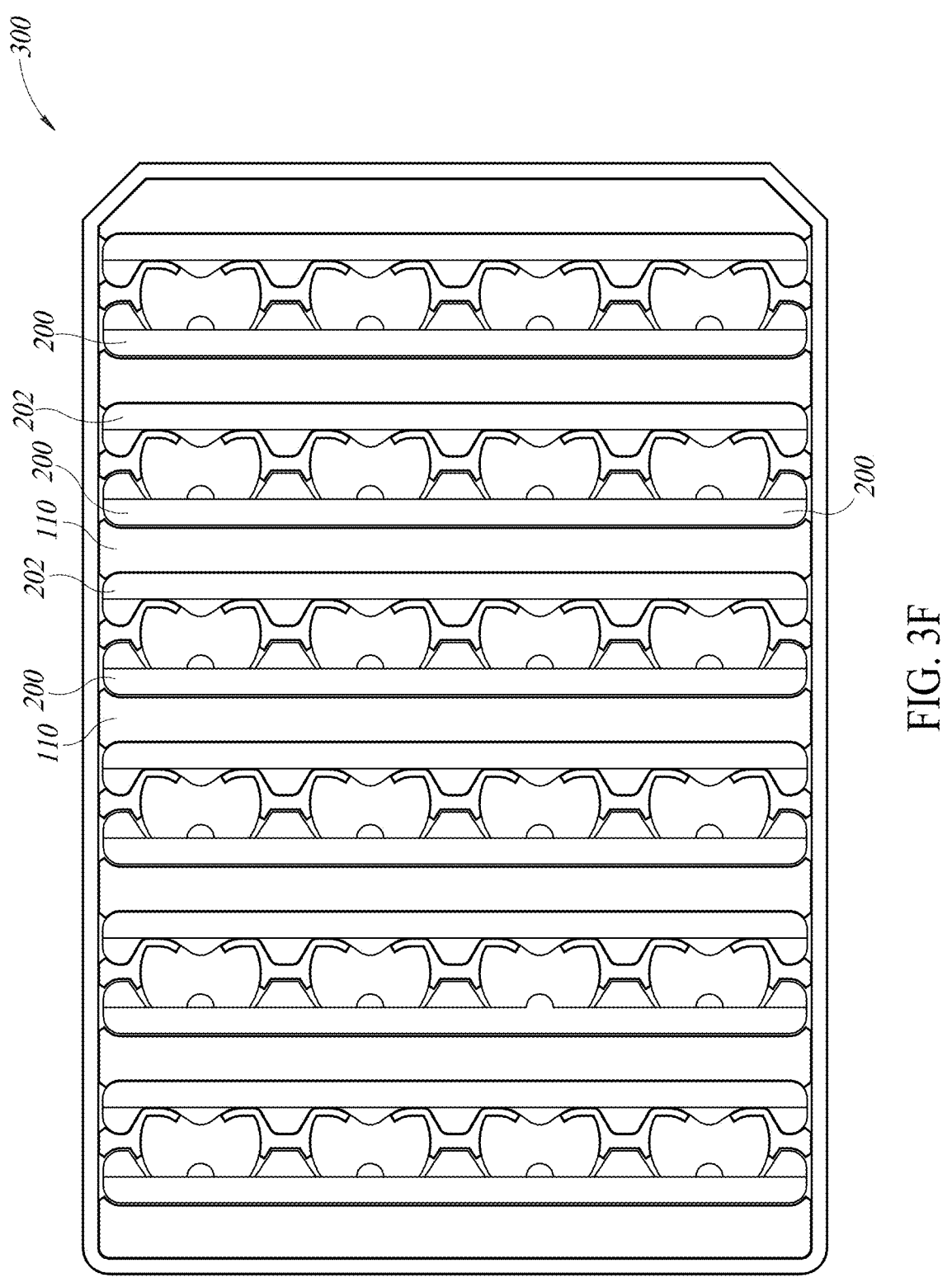
FIG. 3F is a top isometric view of the ET assembly fully assembled.

FIG. 3F shows the assembled ET assembly 300 fully assembled such that each row includes rigid and flexible post assemblies 200, 202 as described above ready for coupling to a casting plate 400.

It should be noted that in another embodiment, the rigid post assembly 200 in each pair of posts may be exchanged for a flexible post assembly 202 (or 204) such that pairs of flexible posts are positioned opposite each other for growing tissue constructs. This may be preferable in some scenarios, although use of a rigid and flexible pair may improve signal strength since the one flexible post deflects the entire length of the tissue contraction, as opposed to with two flexible posts, where each flexible post deflects only half the length. In particular, although the use of a rigid-flexible pair can be advantageous as such a design improves the signal strength of measured contractility of ETs when used in conjunction with a magnetometer-based contractility measurement system (as disclosed by Sniakdecki et all) as the single flexible post deflects the entire length of the tissue contraction, as opposed to with two flexible posts where each post deflects only half the length, two flexible post configuration can be useful in optical imaging-based assay schemes or when other types of assays could be preferably carried out in a more pliable in-vivo like environment.

In another embodiment, ET mounting lid 100 and rigid post assembly 200 are made from the same material formed from a monolithic part (or body), thereby improving manufacturing efficiency. Also, while the preferred means of mounting the rigid and flexible post assemblies 200, 202, 204, is by insertion of the pins 212a or 212b, rigid and flexible post assemblies 200, 202, 204 may be affixed to the ET mounting lid 100 using any means, including adhesives, sealants, clamps, overmolded mechanical interlocks, among others, or any combination thereof.

Figure 4A:
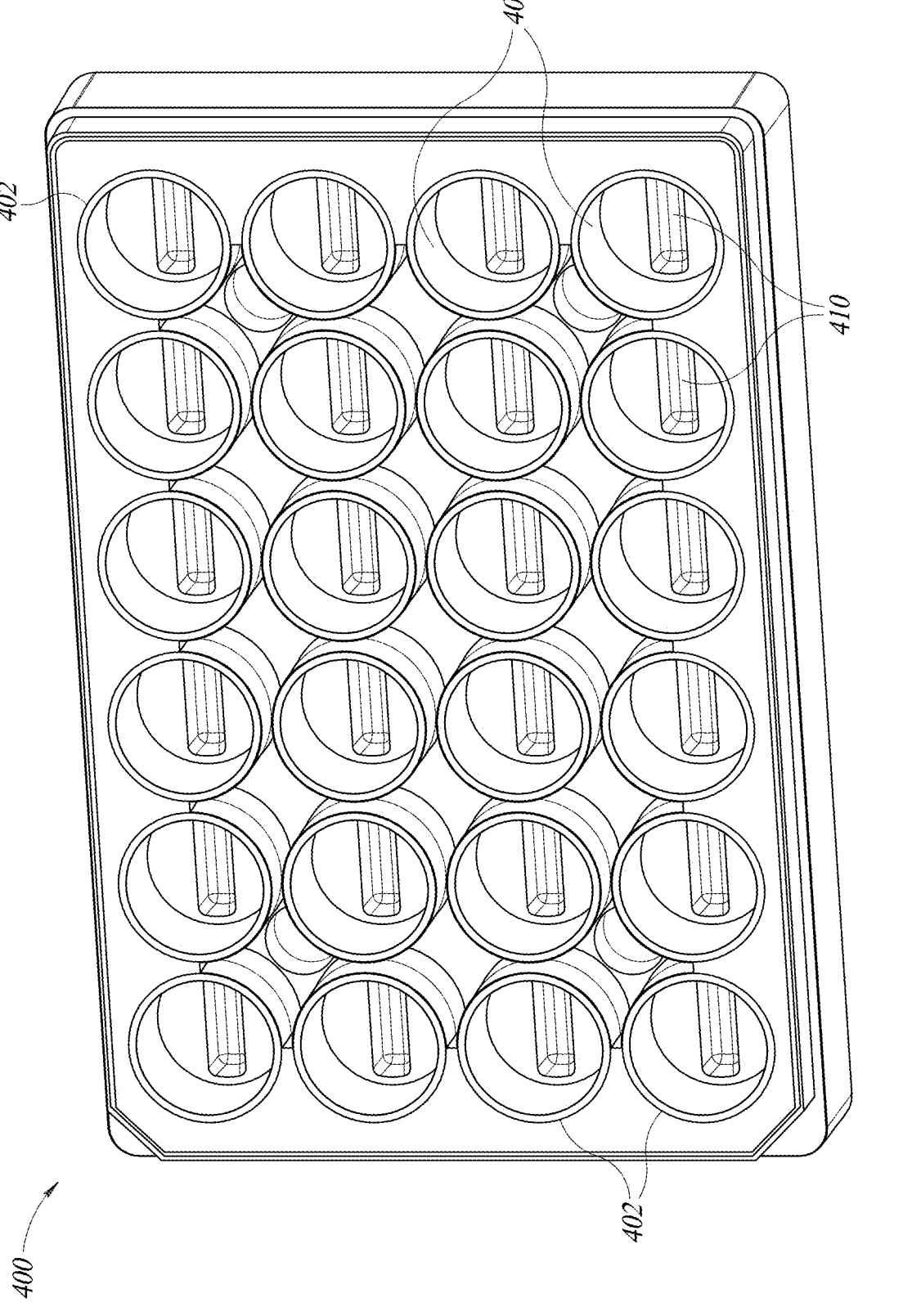
FIG. 4A-4C show various views of a casting plate in accordance with one embodiment.
Figure 4B:
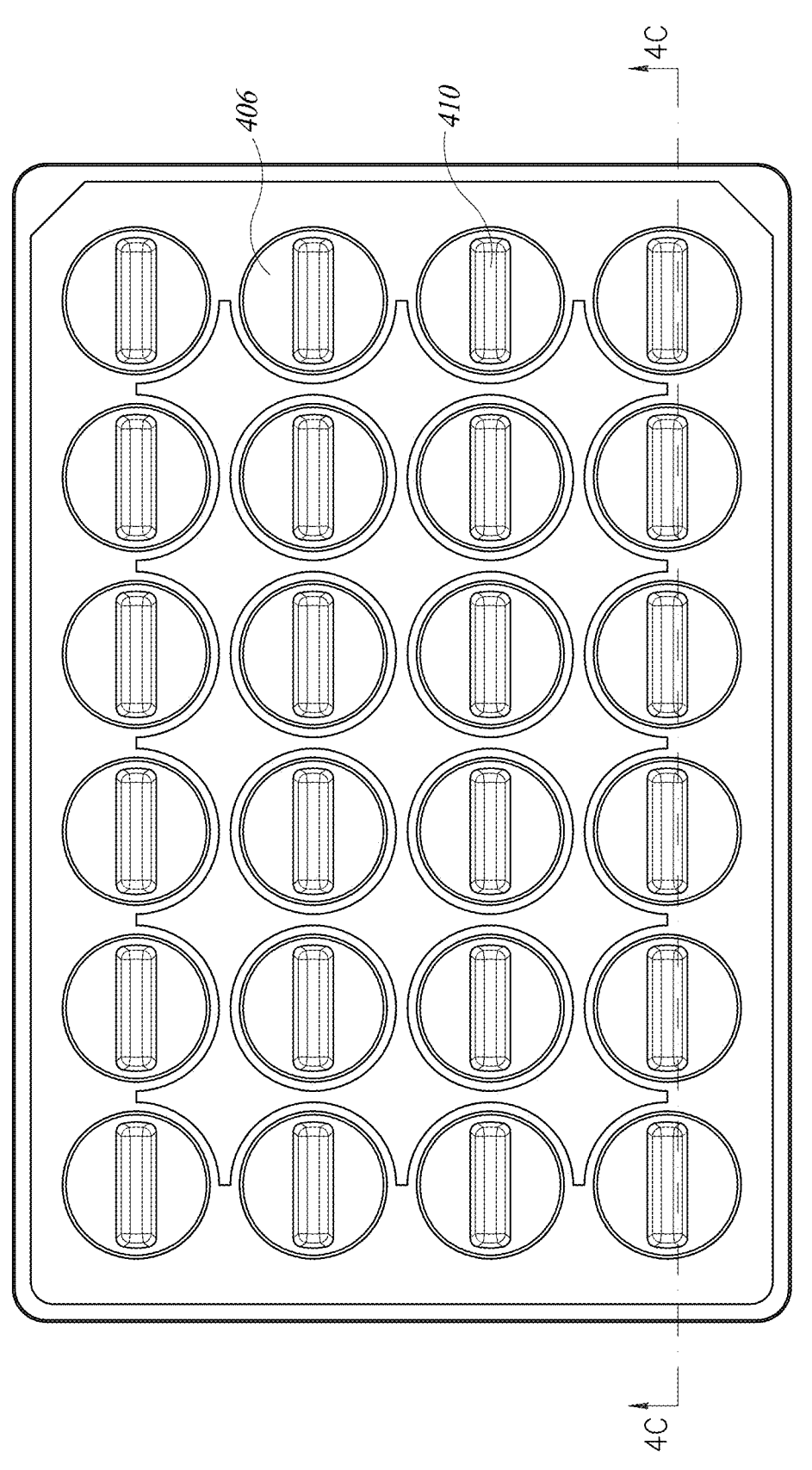

FIG. 4A is a top isometric view of a casting plate 400 (or microplate) in accordance with one embodiment. FIG. 4B is a top view of the casting plate 400 of FIG. 4A, showing a cross sectional line for the cross section view of FIG. 4C. The casting plate 400 includes an array of casting wells 402 for casting tissues to generate ETs that adhere between a pair of rigid and flexible posts of the ET assembly 300 of FIG. 3F. The array of casting wells 402 corresponds to the array of through openings of the ET mounting lid of the ET assembly.

The casting plate 400 comprises casting wells formed by a first portion 404 having an array of bottomless wells 406 and a second portion 408 having an array of recessed wells 410. The bottomless wells 406 are circular shaped in plan view, and the recessed wells 410 are rectangular shaped in plan view. In the illustrated embodiment, the first portion 404 and the second portion 408 are separated components; however, in another embodiment, the bottomless wells 406 and the recessed wells 410 may be formed in a single component, as shown in FIG. 4D.

Figures 4C, 4D:
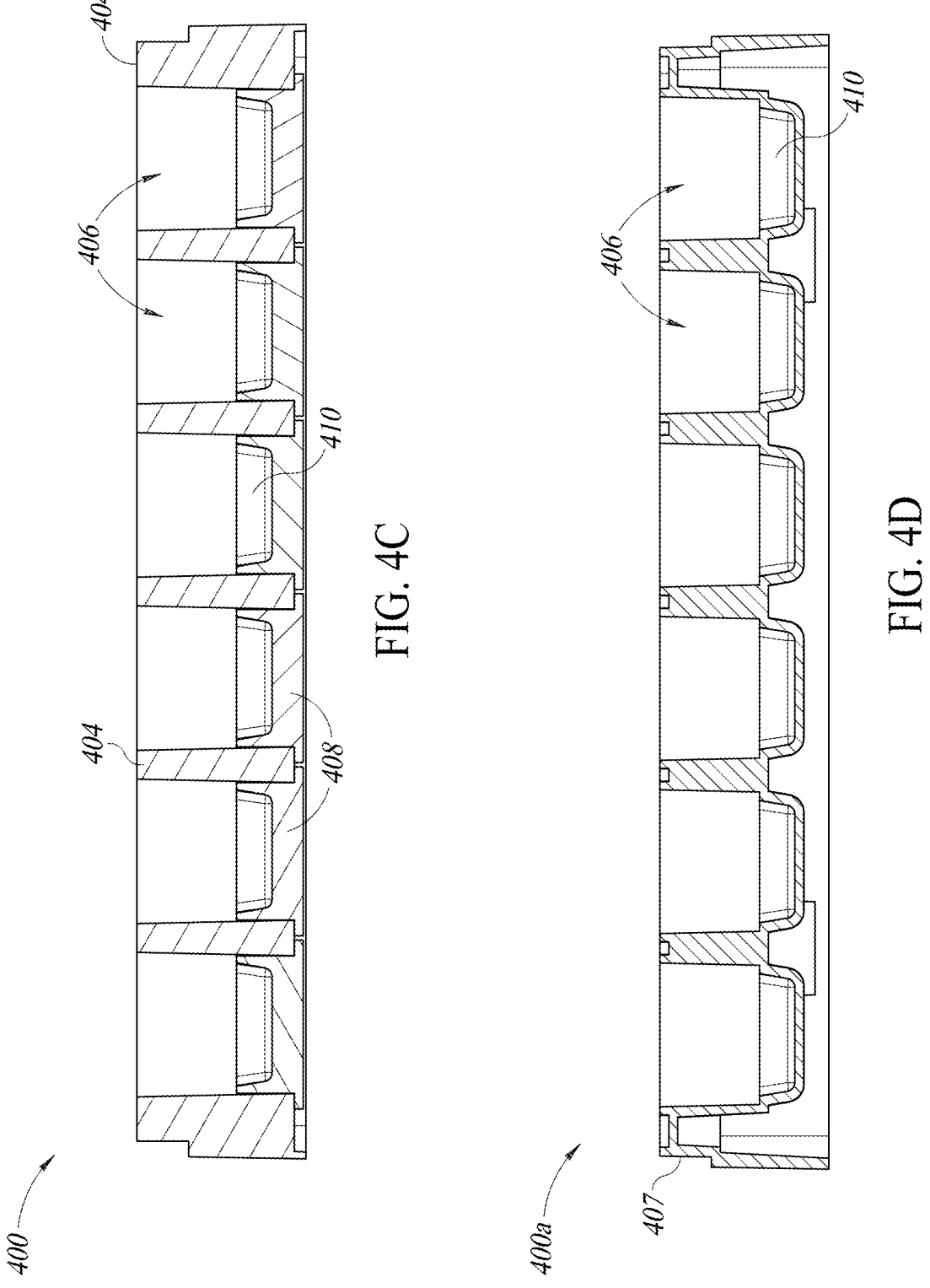
FIG. 4D is a cross section of a casting plate in accordance with another embodiment.

As best shown in FIG. 4C, laterals walls in the recessed wells 410 are sloped at an angle such that the areas of the openings at the recessed wells 410 proximate the bottomless wells 406 are greater than areas at bases of the recessed wells 410. Furthermore, the corners at the bottom of the recessed wells 410 are curved or chamfered. The sloped lateral walls and/or the curved or chamfered corners of the recessed wells 410 aid in allowing the removal of casted tissue therefrom and/or inhibit bubbles from forming during the tissue casting process. In some embodiments, the casting plate 400 is an injection molded part made of polypropylene, which further inhibits tissue from sticking to walls of the wells. While recessed wells in this embodiment are rectangular, they may take other shapes as the situation demands, such as an ovular, dogbone shape, or any other suitable shape FIG. 4C shows cross section of an alternative embodiment of a casting plate 400a.

The casting plate 400a is the same as the casting plate 400 of FIGS. 4A-C except that the bottomless wells 406 and recessed wells 410 of the casting wells are formed in a monolithic body 407.

Figure 5A:
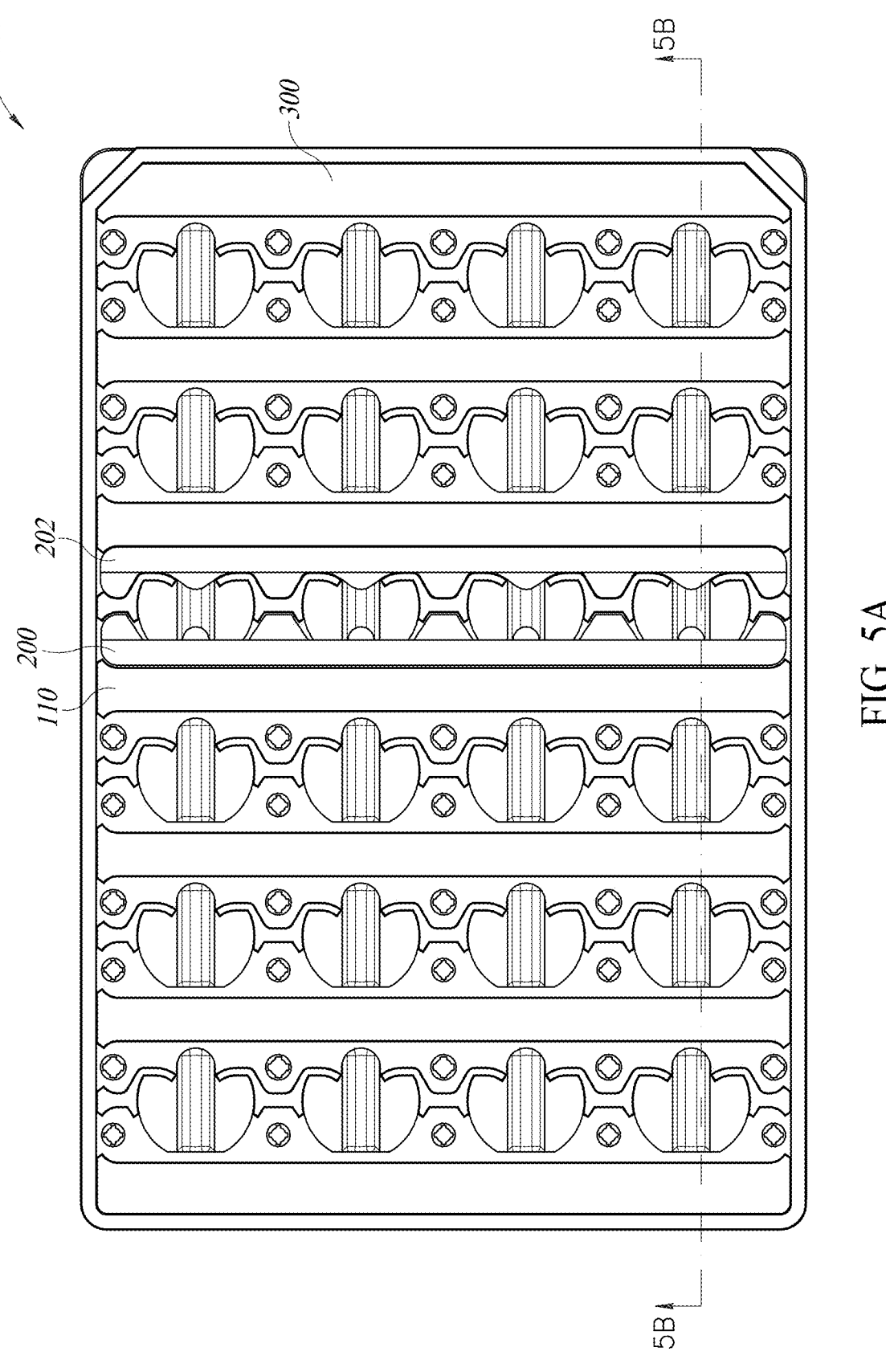
FIG. 5A-5C show various views of a casting assembly comprising the ET assembly of FIG. 3A coupled to the casting plate of FIG. 4A.
Figures 5B, 5C:
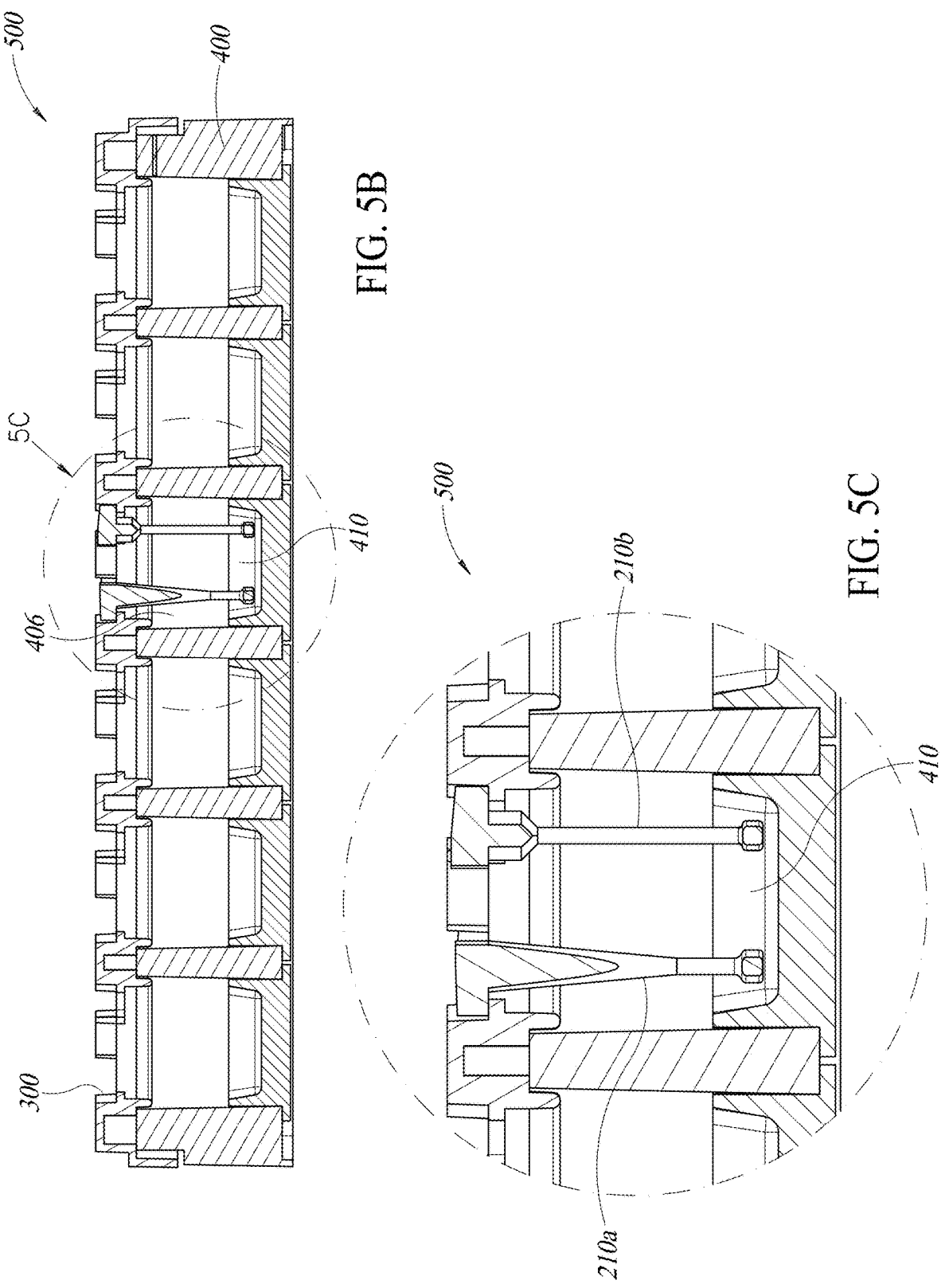

The upper surface of the casting plate 400 (or 400a) is configured to abut with or removably coupled to the ET mounting assembly 300 to form a casting assembly 500 as shown in FIGS. 5A-5C. A partially formed ET mounting assembly is be ng shown in FIGS. 3A-3E to not obscure details of the invention; however, it is to be understood that the fully assembled mounting assembly of FIG. 3F would typically be coupled with the casting plate 400 to form the casting assembly 500.

FIG. 5A is a top view of the casting assembly 500 comprising the ET assembly 300 of FIG. 3A removably coupled to the casting plate 400 of FIG. 4A. FIG. 5B is a cross section view of the casting assembly 500 of FIG. 5A at the cross section line shown in FIG. 5A. FIG. 5C is a close up view of a portion of the casting assembly 500 of FIG. 5B.

As best shown in FIG. 5B, the second side 102b of the ET assembly 300 is removably coupled to the upper surface of the casting plate 400 such that an outer surface portion of the ET assembly 300 rests in a recess of the outer surface portion of the casting plate 400.

The casting wells, that is, the bottomless and recessed wells 406 410, of the casting plate 400 are aligned with the through openings of the ET assembly 300 such that the pairs of rigid and flexible posts 210a, 210b are received in the casting wells, extending through the bottomless wells 406 and into the recessed wells 410. Although only a single pair of rigid and flexible posts are shown, it is to be understood that each casting well would include a respective pair of rigid and flexible posts.

As previously mentioned, the protruding rings 113 of the ET mounting lid 100 provide an alignment feature for coupling the ET mounting lid 100 to the casting plate 400. In particular, the protruding rings 113 align the ET mounting lid to the casting wells of the casting plate such that posts of the ET assembly are aligned in a center region of the casting wells, thereby providing a more consistent alignment and allowing for automated placement, as well as more consistent morphology from tissue to tissue. This improved tissue consistency provides for more reproducible magnetic sensing, imaging, and anything else that requires consistent placement. Since these protruding rings 113 allow more accurate and consistent placement of ET assembly 300, not only on the casting plate 400, but also on any other tissue culture plate, with the proper form factor, they more consistently align tissues affixed to ET assembly 300 with any sensor used to evaluate these tissues, giving more consistent and reproducible data.

Although not shown in cross sectional view of FIGS. 5B and 5C, the pegs 114 provide an alignment feature that aids in aligning the ET assembly 300 when placing the ET assembly 300 on the casting plate 400. Due to the pegs 114 being longer than the rigid and flexible posts 210a, 210b, ends of the rigid and flexible posts 210a, 210b or any tissue formed therebetween may be protected from impacting the casting plate 400 as ends of the pegs 114 will be received in respective openings in the casting plate 400 before ends of the rigid and flexible posts 210a, 210b are received in the bottomless wells 406 of the casting plate 400.

In operation, tissue solution is provided at the through opening 104 of the ET assembly 300, which is received in recessed wells 410, wherein tissue casts between the pairs of the posts in each casting. After the tissue solution has gelled sufficiently, it can be removed from the casting plate by removing ET assembly 300 from the casting plate. ET assembly 300 may then be placed upon any other appropriate tissue culture microplate for long-term culture of the tissues affixed thereupon. There may be some situations in which the tissue must gel for long periods of time within a recessed well 410, in which case bottomless wells 406 may provide a reservoir for additional nutrient medium to sustain the tissue over this duration.

The various components of the casting assembly 500 allow for improved manufacturability, including automated handling, of the various compo ents improving the manufacturability of tissue casting, including muscle tissue, nervous tissue, or combinations thereof.

Figure 6A:
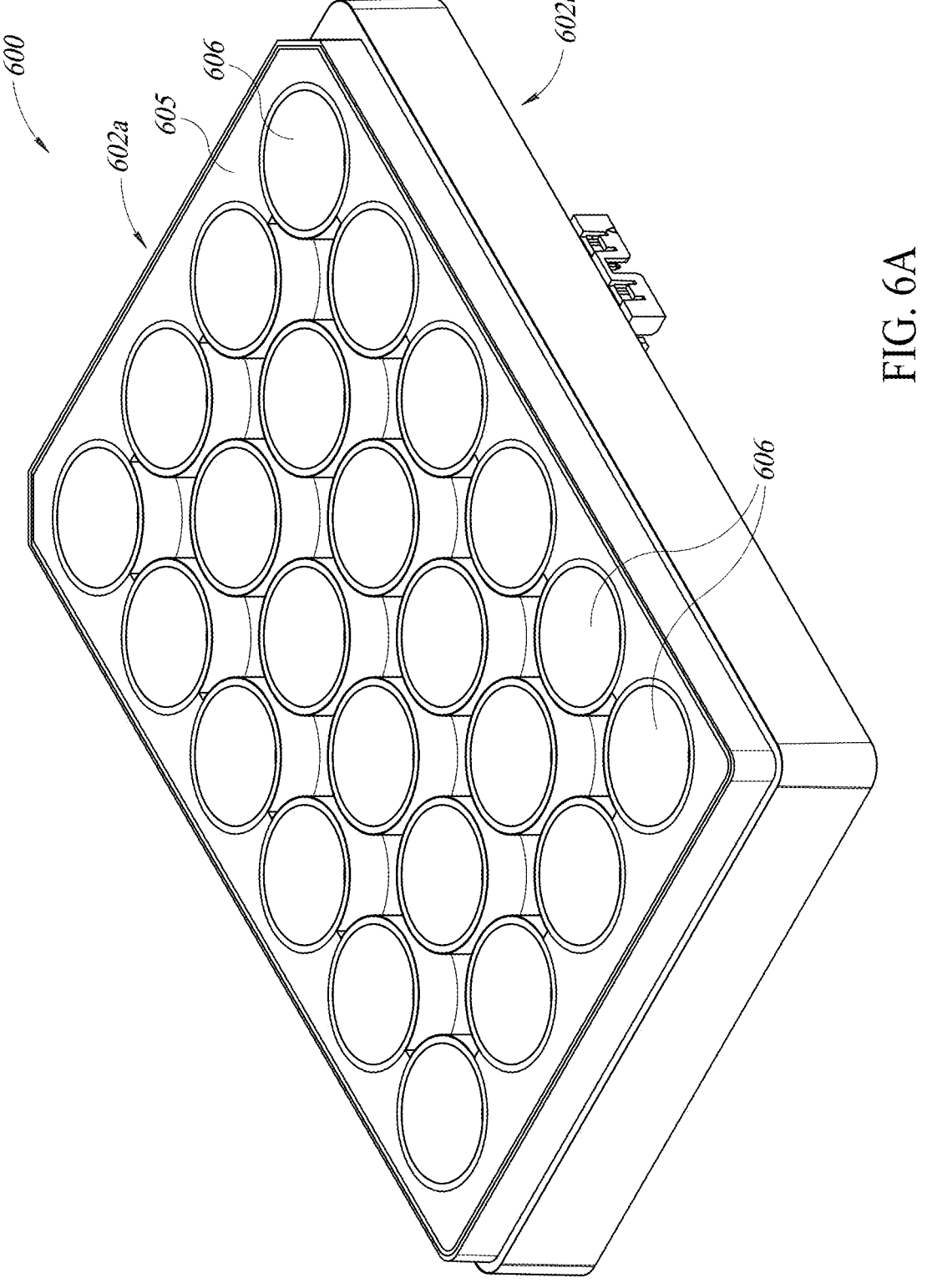
FIG. 6A-6C show various views of a stimulation plate for electrically stimulating tissue constructs in accordance with one embodiment.
Figure 6B:
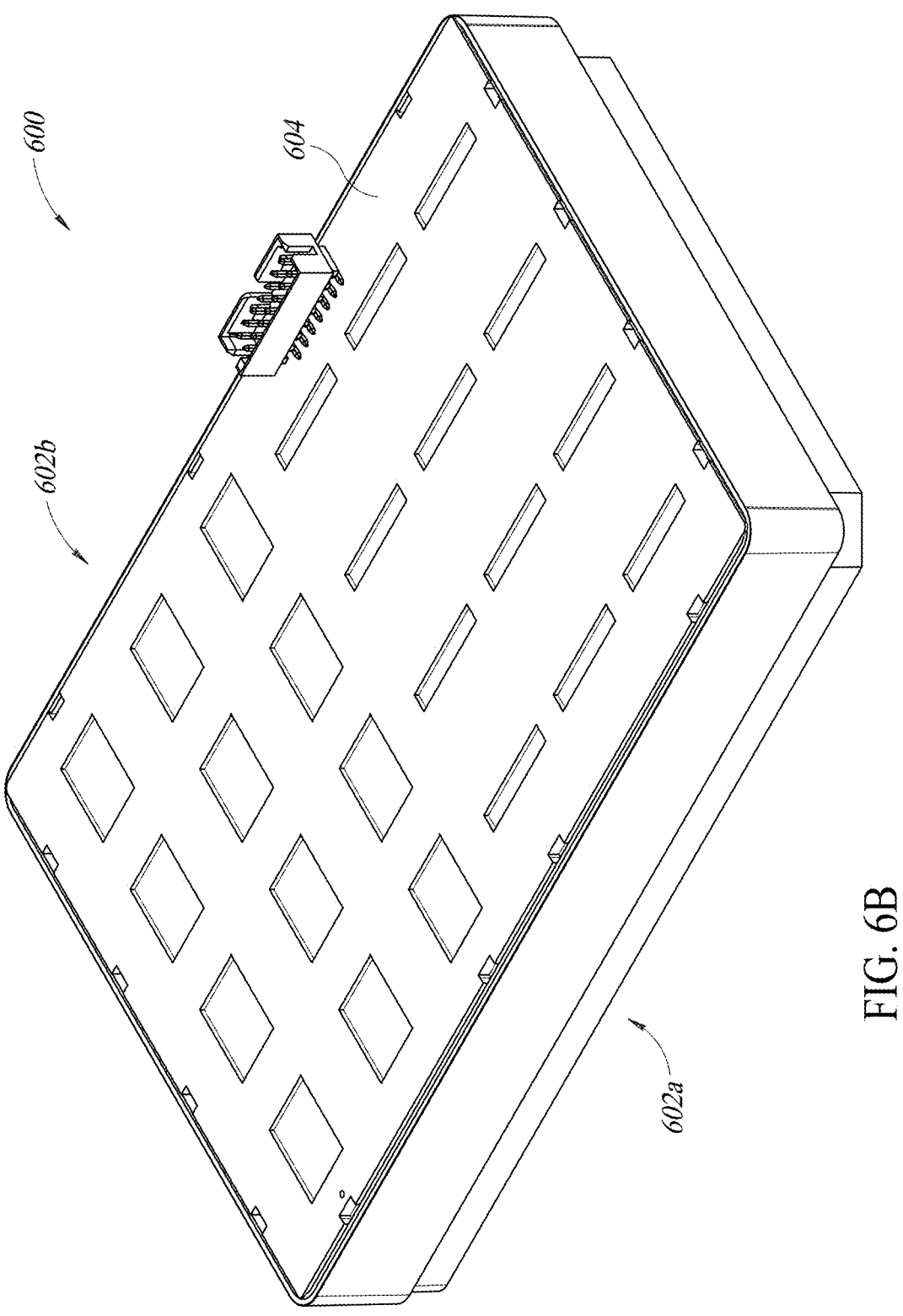

Electrical stimulation can be used to induce more maturation or physiological development of the ETs. Cells and tissue that have grown in the casting process in each respective recessed well 410 (and in some cases in the bottomless well 406) and remain adhered to ET assembly 300 after removal from the casting plate 400, may be exposed to electrical stimulation. FIGS. 6A and 6B show opposing sides of a stimulation plate 600 (or an electrical plate assembly) for applying electrical stimuli to the cells and tissues of 3D ETs, such as engineered heart tissue (EHT). FIG. 6A shows a top isometric view of the stimulation plate 600, FIG. 6B shows a bottom isometric view, and FIG. 6C shows the stimulation plate 600 in cross section.

The stimulation plate 600 includes a backing plate 604 and a body 605 comprising a plurality of bottomless wells 606 that correspond to the through openings of the ET assembly 300. The backing plate 604 is a rigid backing plate that is coupled to the body 605, such as by any suitable bonding or adhesive material. In the illustrated embodiment, the backing plate 604 comprises a printed circuit board (PCB) with conductive elect odes 610a, 610b (FIG. 7B), such as gold, on a first side that are in electrical connection with a connector. The conductive electrodes 610a, 610b on the first side of the body 605 are aligned with the bottomless wells 606 of the body 605. The PCB may include viewing windows 612a and 612b that enable viewing of the contents of the bottomless wells 606 from underneath stimulation plate 600. Different sizes and shapes for the viewing windows 612a, 612b and conductive electrodes 610a, 610b are shown; however, they may all be the same size and shape or another size and shape than is shown.

Figure 6C:
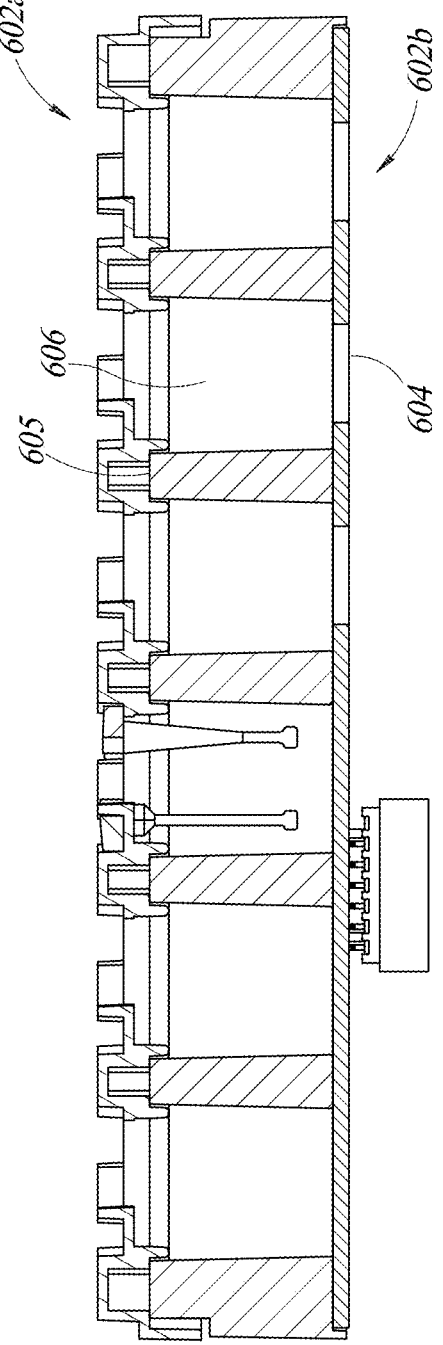

FIG. 6C, shows the stimulation plate 600 in cross section. The plurality of bottomless wells 606 of the body 605 are configured to receive tissue constructs. The cell or tissue constructs are placed in electrical communication with the conductive electrodes 610a, 610b, such as capacitively coupled thereto. Electrical stimuli are used to induce electrophysiological responses to the cell culture or to characterize its responses to drug compounds.

The conductive electrodes 610a and 610b are configured to interface with a stimulator, by conventional ways in the art, such as by contact pads or a connector and various traces and vias on the PCB, and an external power source to provide electrical signals thereto. The backing plate 604 may further include a transparent film coupled to the first side 602a of the PCB, such as by any suitable bonding or adhesive material, to thereby seal the bottomless wells of the stimulation plate.

Figure 7A:
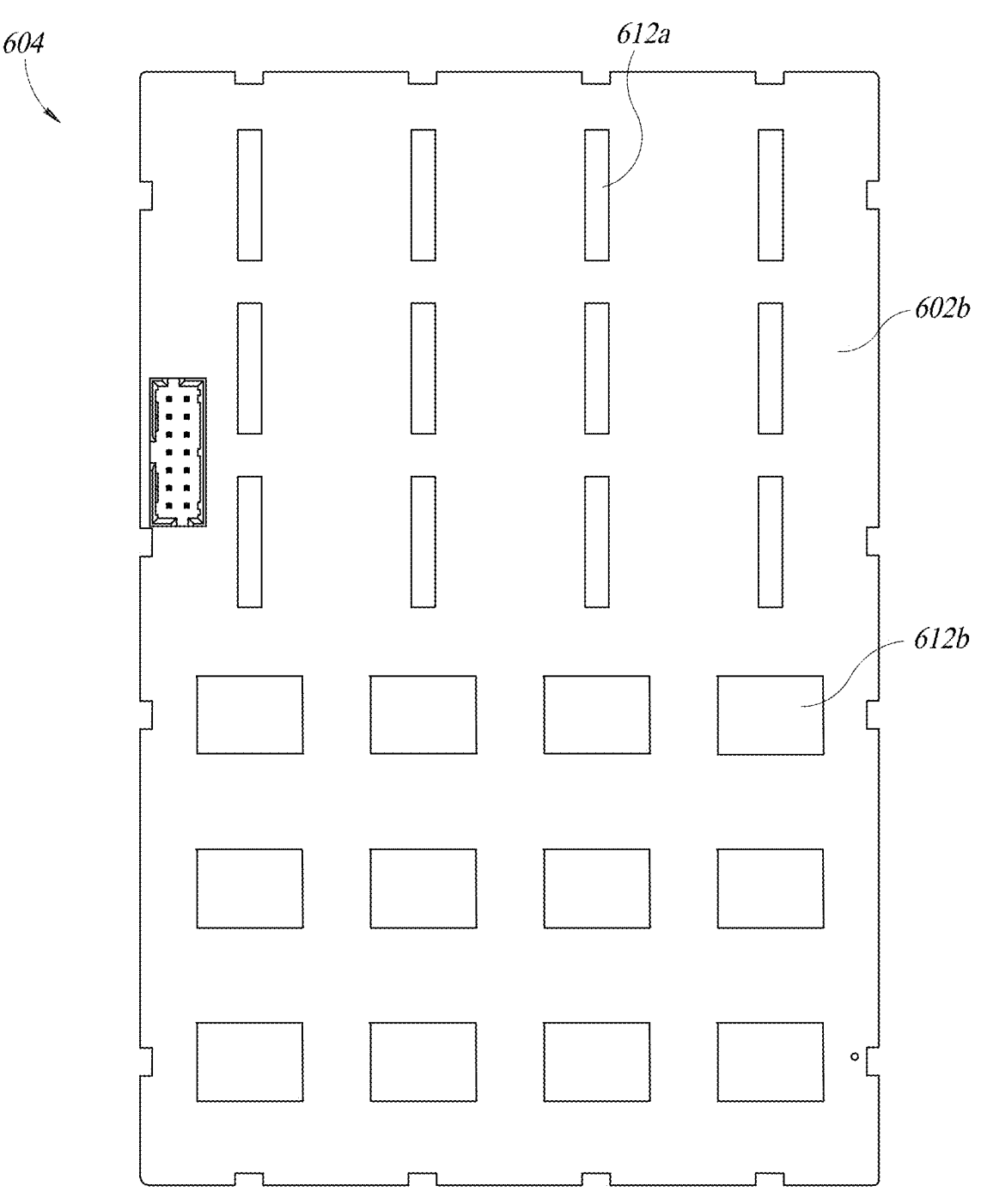
FIG. 7A-7B show various views of the PCB of the stimulation plate of FIG. 6A in accordance with one embodiment.
Figure 7B:
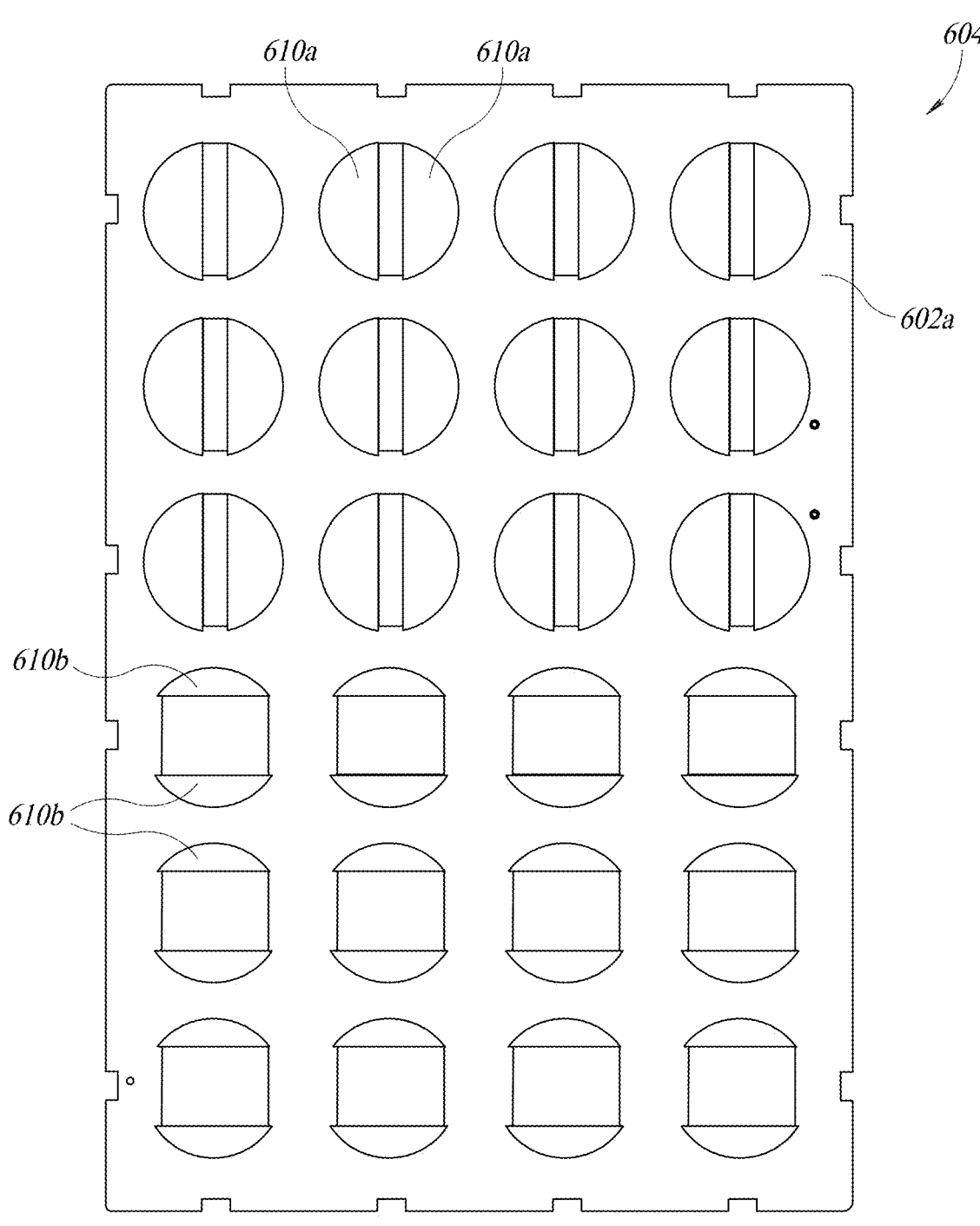

FIGS. 7A and 7B illustrate the PCB of FIGS. 6A and 6B in greater detail. The bottom side of the PCB, as shown in FIG. 7B, has a ground plane and a connector, although the connector may also be on the top side in some embodiments. The connector may be a ribbon connector for coupling to a connector of the stimulator. In other embodiment, instead of a connector, exposed contact pads on second side 6B can also be used to couple to conductive electrodes 610a and 610b to the stimulator to provide sufficient current low through each well in the respective row of wells in the stimulation plate.

Figure 8A:
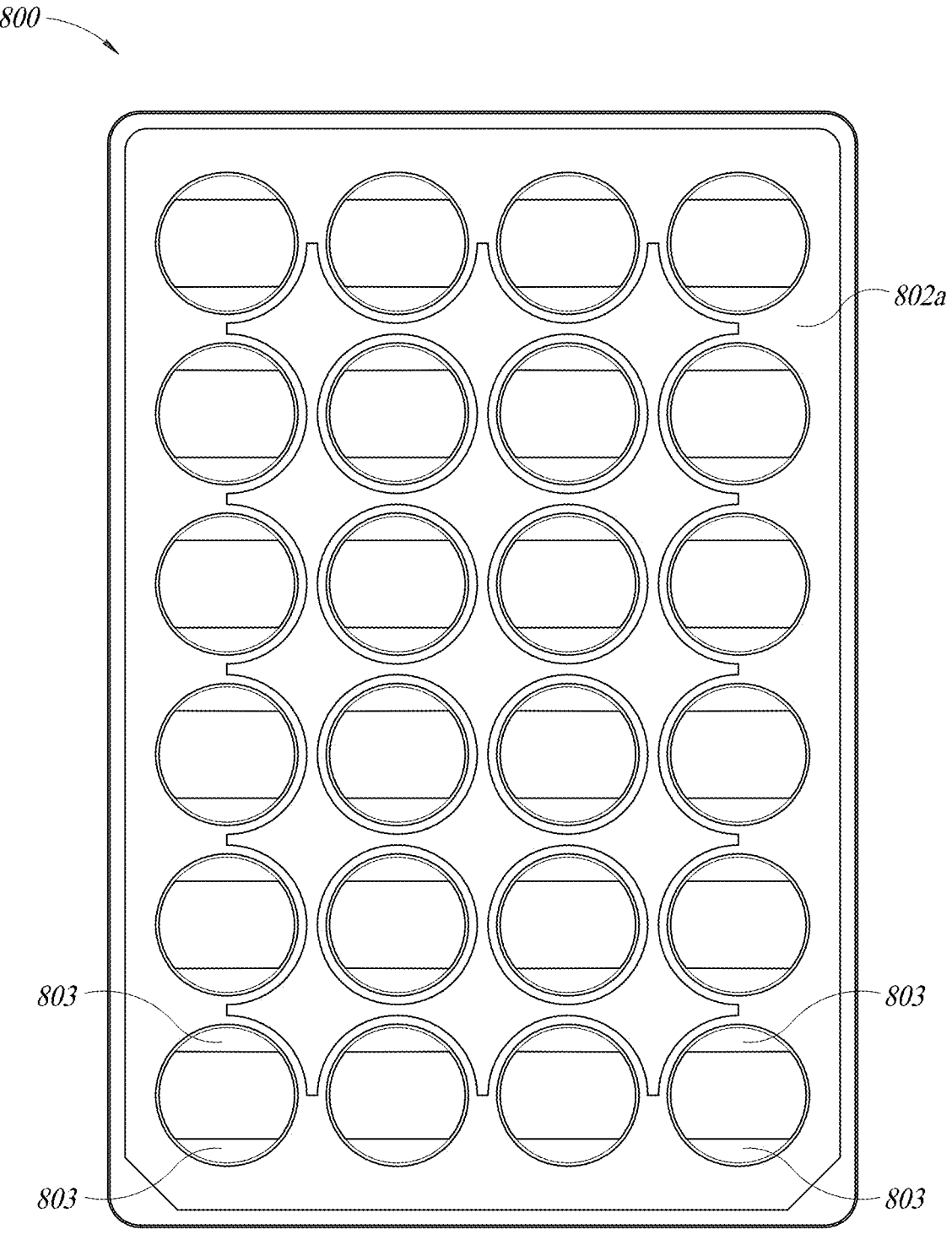
FIG. 8A-8B show various views of the PCB of the stimulation plate of FIG. 6A in accordance with another embodiment.
Figure 8B:
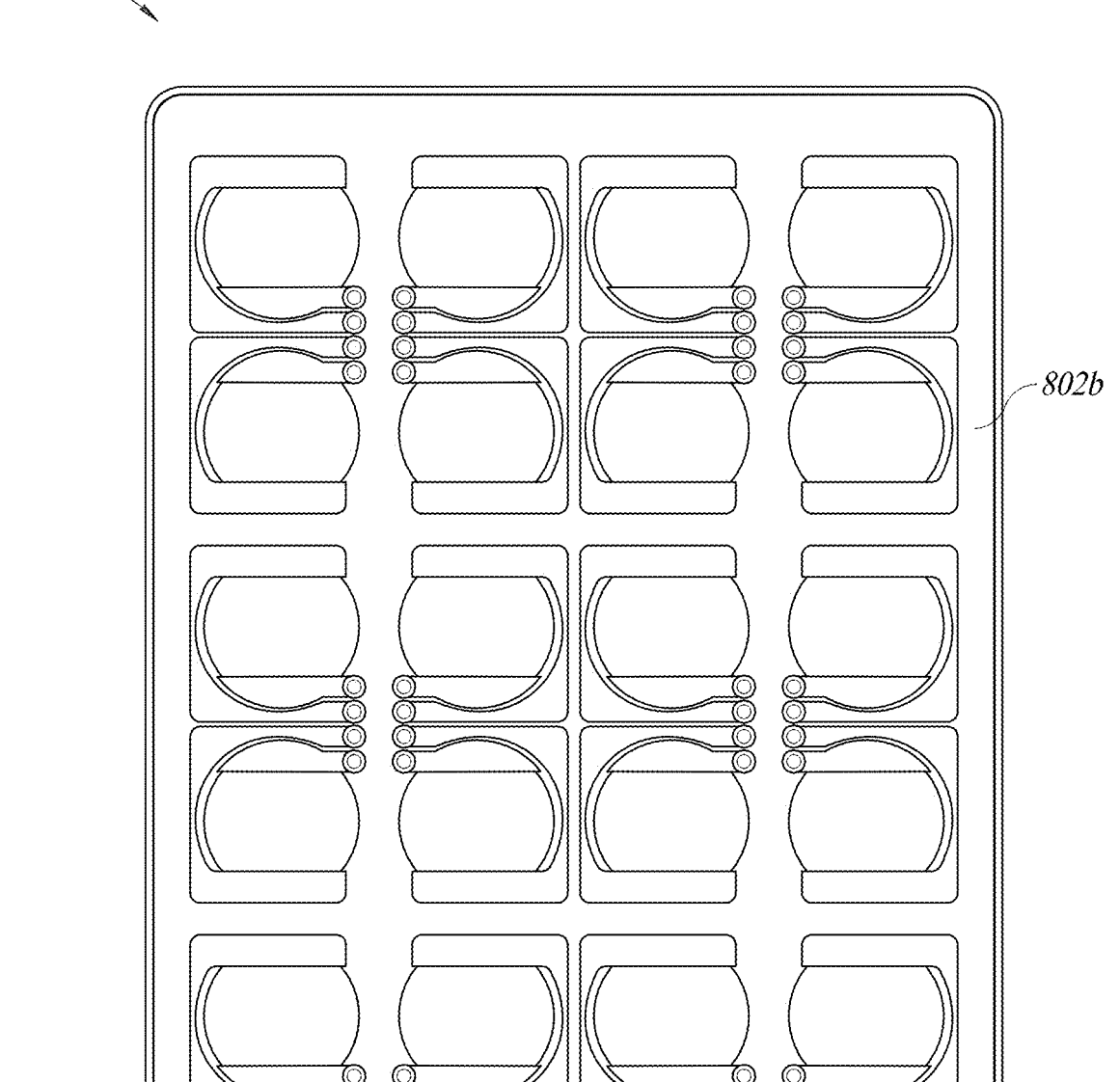

FIG. 8A illustrates an alternative backing plate for the stimulation plate 600. FIG. 8A is a plan view of a first surface 802a of a backing plate 800 of a stimulation plate, while FIG. 8B is a plan view of a second surface 802b of the backing plate 800. In this embodiment, the stimulation plate 800 comprises a transparent plastic film 802, although in other embodiments this film may be made from translucent or opaque films such as polyimide. The first surface 802a is formed by the transparent plastic film 802 and conductive electrodes 803 that are arranged in pairs. The first surface 802a is configured to be directly bonded, by any suitable bonding or adhesive material, to the body 605 such that the conductive electrodes 803 are aligned with the bottomless wells 606 of the body 605.

The second surface 802b of the backing plate 800 includes electrical contacts 805 that are coupled to the conductive electrodes 803 of the first surface 802a by vias and traces as is well known in the art. The transparent film acts as a seal for the tissue constructs which may be provided within the bottomless well 606 of the body 605. Each bottomless well 606 of the body 605 may be electrically isolated or many wells, such a row of wells, may be electrically coupled together by traces. The conducting electrodes 803 may have geometries best suited for the given application, such as the shown semicircular pattern, but also serpentine and fractal geometries may be used. The conductive material may be metal, ceramic, polymeric material, conductive paste, or a mixture or layering thereof. Some examples of these materials include Gold, Platinum, Graphite, Carbon Nanotubes, PEDOT, PEDOT PSS, Indium Tin Oxide, and Sputtered Iridium Oxide, which can enhance charge injection capabilities of the electrodes.

For testing, the 3D tissue constructs formed on the pairs of the rigid and flexible posts on the ET assembly 300 are inserted into each bottomless wells 606 of the body 605 of the stimulation plate 600. Stimulating the tissue cultures from the bottom of a tissue culture plate provides an improved testing method over the prior art, in that they can be efficiently manufactured using industry standard processes and are easily replaceable.

Another embodiment provides a direct substrate-based stimulation plate that can be used to replace the backing plates. The sizes and/or layout of stimulation electrodes on the backing plate can be configured in any format that are designed to optimize electrical stimulation of various types, sizes, shapes or assemblies of tissues. In one further embodiment, the electrode pattern on the backing plate could have a direct substrate-based electrical stimulation design with electrically conductive material of very low electrical impedance, such as PEDOT:PSS, that covers a large surface area of the substrate.

Figure 9A:
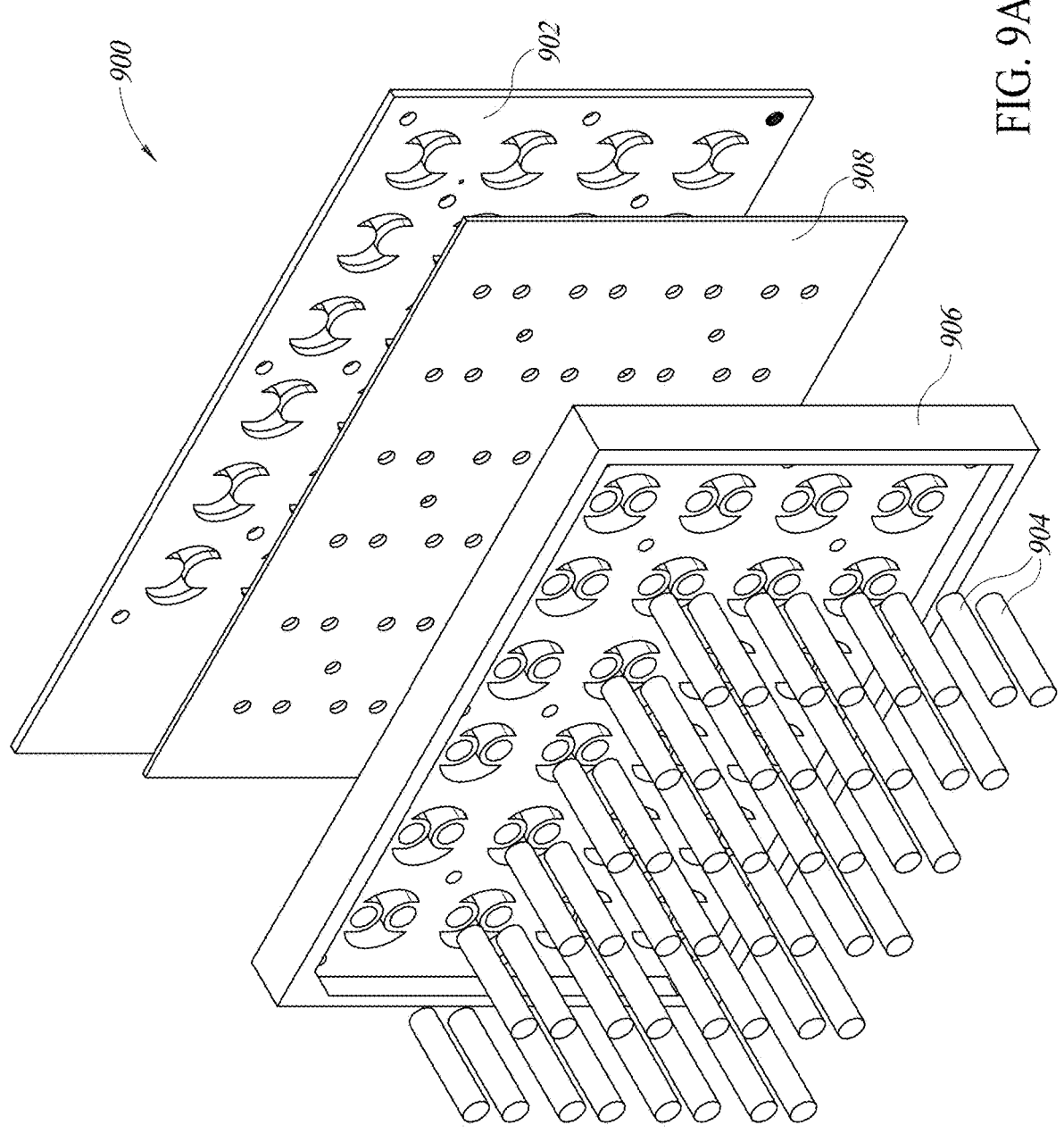
FIG. 9A is an exploded view of the stimulation lid in accordance with one embodiment.
Figure 9B:
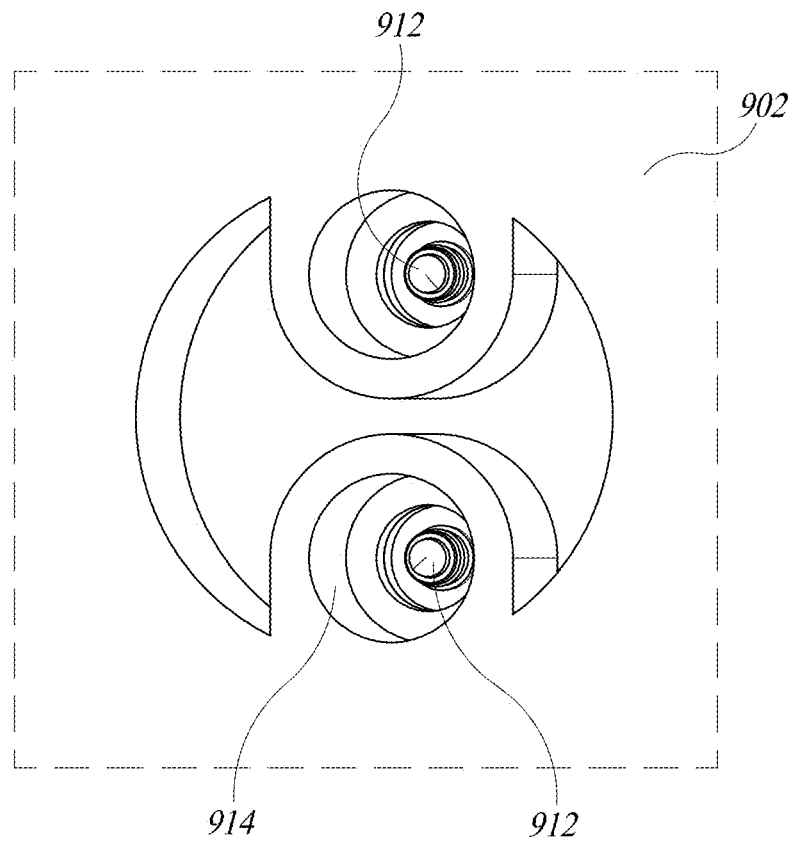
FIG. 9B is a close up view of the PCB of the stimulation lid of FIG. 9A.
Figure 9C:
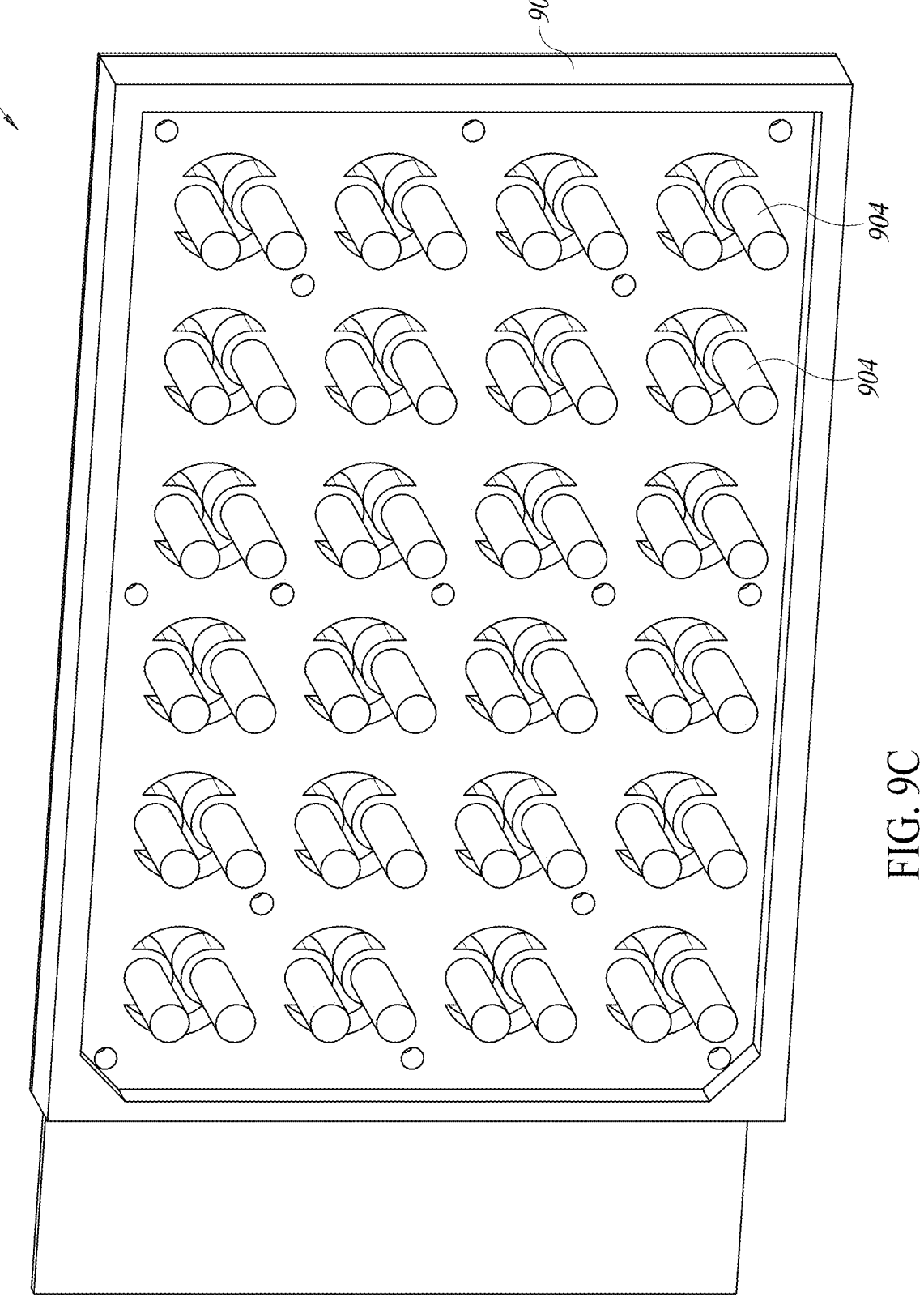
FIG. 9C is a bottom view of the stimulation lid of FIG. 9A fully assembled.

Conventional electrical ET stimulation devices are stimulation lids that utilize rod electrodes protruding downward from the top of a tissue culture microplate into the media bath of each well to stimulate tissue cultures therein. FIGS. 9A-9C illustrate an improvement to electrical stimulation lid 900 that utilizes rod electrodes 904 that protrude downward into a microplate. The stimulation lid 900 applies electrical stimuli to the cells and tissue constructs affixed to the ET assembly 300. FIG. 9A shows an isometric exploded view of each component of the stimulation lid 900, while FIG. 9C shows a bottom view of the stimulation lid 900 fully assembled.

With reference to FIG. 9A, the stimulation lid 900 comprises a printed circuit board (PCB) 902 configured to couple with a connector of an external electrical stimulator or that incorporates an electrical stimulation module on-board.

The stimulation lid 900 further comprises a plurality of removable rod electrodes 904, such as graphite rod electrodes or any other suitable material, arranged in pairs and in electrical connection with the PCB 902. In one embodiment, the rod electrodes 904 are 3/16 inch in diameter; however, smaller or larger diameter electrodes, or non-rod-shaped electrodes may be used in other embodiments.

First ends of the electrodes 904 are coupled to the PCB 902 by contacting and pressing against pogo pins 912 on the PCB 902. FIG. 9B shows a partial close up view of a pair of pogo pins 912 located inside respective sockets 914 of the PCB 902 for receiving the electrodes 904. In particular, first ends of the electrodes 904 are received in the sockets 914 and pressed against the spring loaded pogo pins 912 to provide electrical connection to electrical components, such as contacts, pads, vias, and traces, of the PCB 902 as is conventional in the art. The pogo pins 912 mounted onto the PCB 902 establish a reliable electrical connection to the rod electrodes 904 when friction fit into sockets 914. The rod electrodes 904 are removable within the sockets 914 of the PCB 902. Accordingly, the rod electrodes 904 may be individually replaced as needed, thereby enhancing the commercial utility of stimulation lid 900 in high-throughput electrical stimulation studies.

Second ends of the pair rod electrodes are arranged and configured to be inserted into wells of a microplate for stimulating the tissue constructs. The stimulation lid 900 further includes an aligner 906 mechanically coupled to the PCB 902. The aligner 906 includes through openings that are arranged to correspond with or overlap the wells of a microplate so that second ends of each pair of rod electrodes extend into a respective microplate well. In operation, the stimulator provides signals to charge the rods, the signals stimulate the cells and tissue cultures in the wells of the microplate.

Between the PCB 902 and aligner 906 is a gasket 908 made of elastomeric material. The gasket provides a seal to ensure sterility of the tissue cultures within the microplate and below the stimulation lid 900 when the stimulation lid is coupled to the microplate. Gaps between the PCB and aligner may be additionally sealed with curable polymeric material.

Figure 10A:
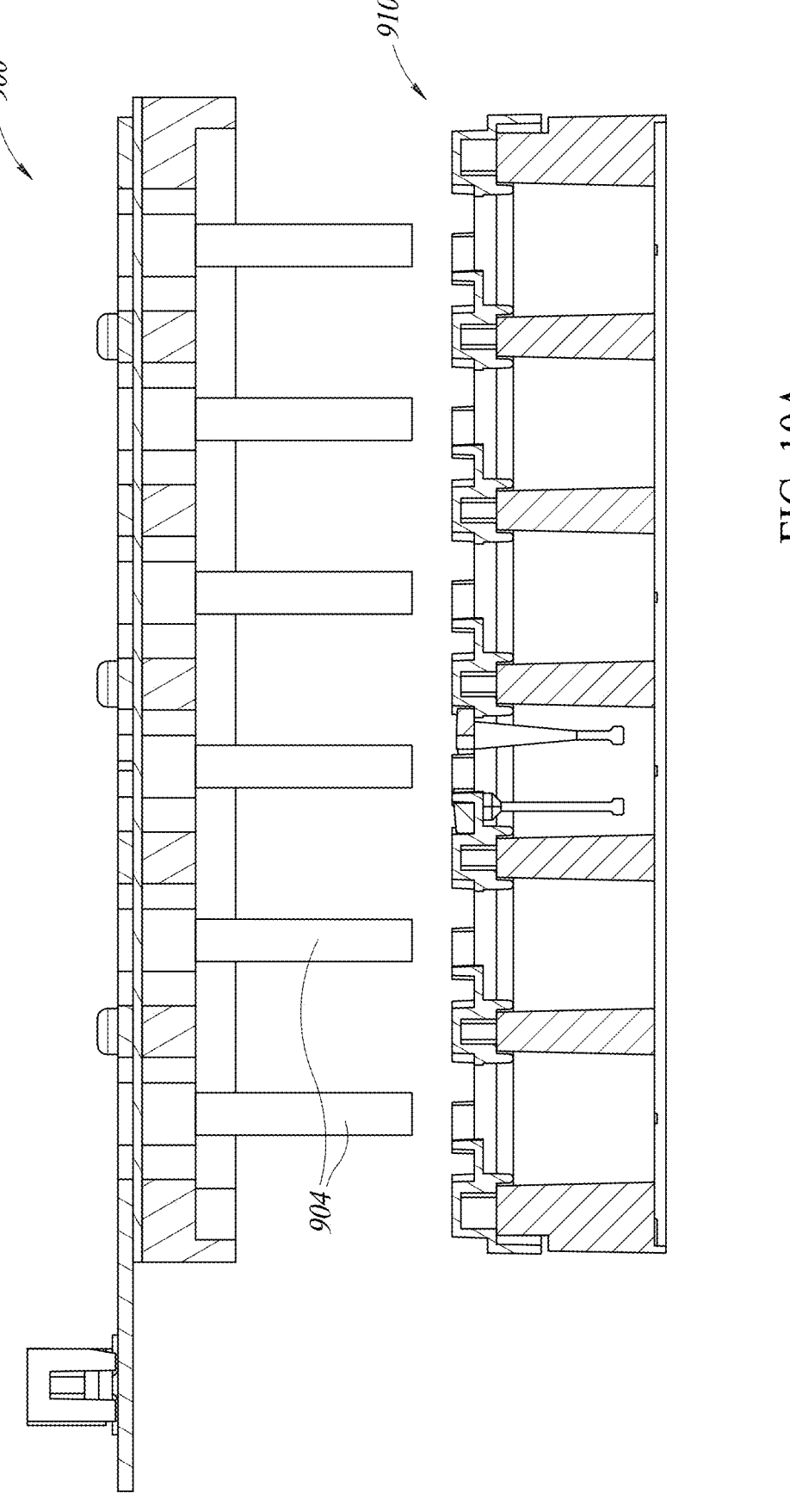
FIG. 10A-10B show various view of a stimulation lid of FIG. 9C about to be installed on a tissue culture microplate.
Figure 10B:
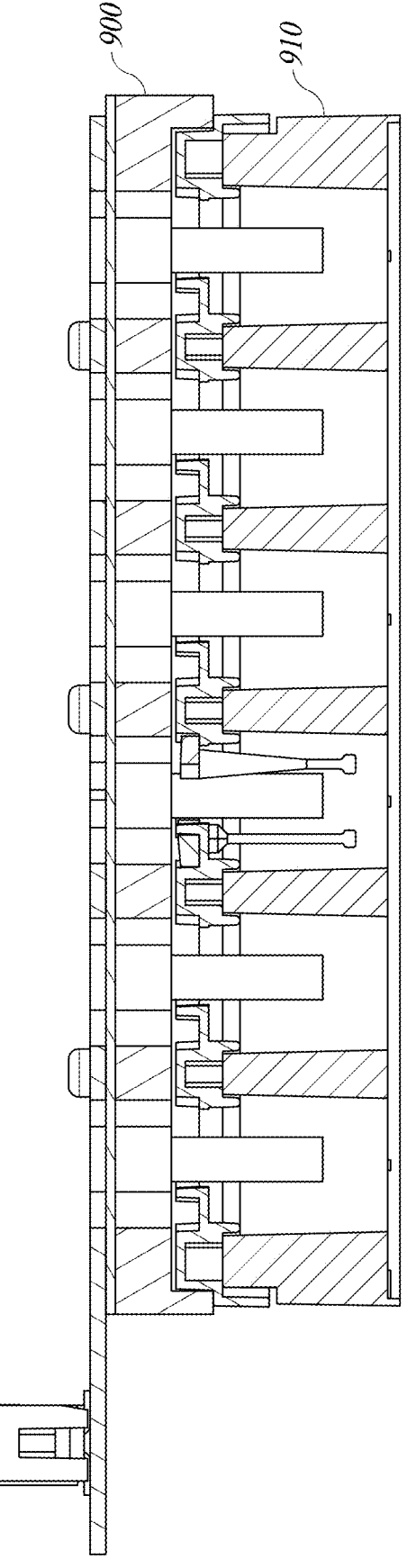

FIG. 10A shows the stimulation lid 900 of FIG. 9C being installed on a partially assembled ET assembly 300 atop a microplate device suitable for tissue culture. The aligner 906 includes a lip at the perimeter that fits with a recess around the perimeter of the microplate device. FIG. 10B shows the stimulation lid 900 of FIG. 9C fully installed on the ET assembly 300 with the lip of the aligner 906 fitting into the recess of the ET assembly 300. As shown in one microplate well, the second ends of the rod elect odes extend through the microplate well toward the tissue constructs. The cell or tissue constructs are in electrical communication with the rod electrodes, such as capacitively coupled thereto. Electrical stimuli are used to induce electrophysiological responses to the cell culture or to characterize its responses to drug compounds.

Figure 11:
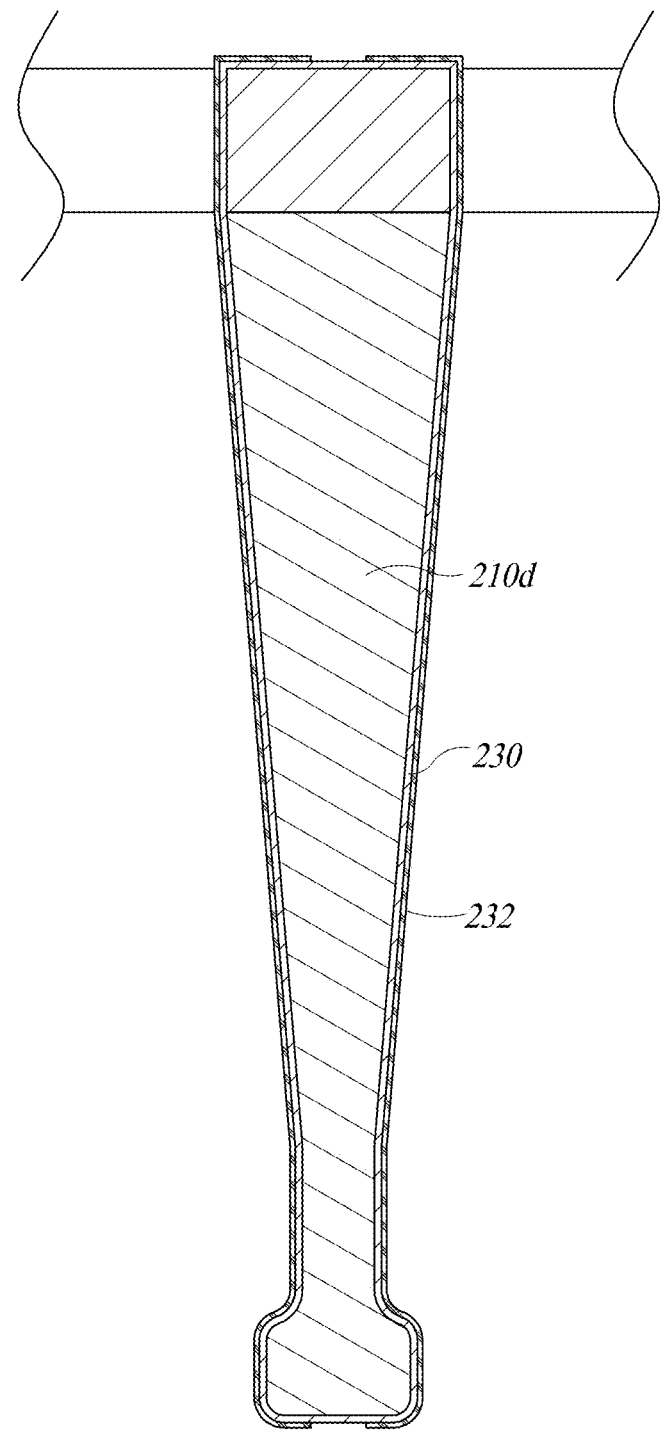
FIG. 11 is a cross section view of a post in accordance with one embodiment.

FIG. 11 shows a post 210d in accordance with another embodiment. The post is identical to the post 210a discussed above, however, the post 210d is coated with one or more layers of electrically conductive material 230, such as a first layer of gold and a second layer of conductive polymer. The conductive layer may extend to the base 208 in order to form an electrical contact pad that can be used to interface with external instrumentation. Although only a rigid post is shown, the flexible posts may also be covered with a layer of an electrically conductive material.

The post 210a coated in 230 may be used to send or record electrical signals to or from the tissue in order to manipulate and evaluate its behavior. Portions of conductive coating 230 may be further covered in an insulating layer 232, thereby limiting the conductive area exposed to the tissue construct. Additional patterning of the conductive layer 230 can be performed to form multiple tracks that can record or stimulate electrical activity ETs from multiple points independently.

The one or more electrically conductive layers, or the tracks of such conductive layer, of the posts (more particularly, flexible posts) may be formed with flexible electrode materials. One example of such flexible electrode arrays that can be formed on the posts is disclosed on the website of a commercial company, BMSEED (www.bmseed.com), which is incorporated herein by this reference. Additionally, such a conductive layer or the tracks thereof could be configured to work with an external system for measuring electrophysiology of the ETs (with electrical stimulation or without stimulation), separately or in conjunction with the measurement of contractility of the ETs.

The consumable device of the present invention is uniquely designed to reduce variability in the ET casting process. Current tissue-casting protocols are academic in nature. These protocols are highly technical and difficult to transfer the technology to other users in a way that is reproducible, even with extensive expertise. The ET assembly and the casting assembly of the present invention allows for the production of highly consistently-shaped tissues that are aligned in the center of each casting well. This allows for the robust formation of 3D ETs that completely wrap themselves around each post and reduces variability associated with misalignment during the tissue casting process. The unique design of the trenches in the casting wells also allows for the successful transfer from the casting wells, where they are allowed to gel, to their respective tissue culture plates containing medium for growth. This is absolutely critical, as newly-formed tissues are delicate and any slight adherence to the casting substrate can cause catastrophic failure of the ETs cast. Additionally, the design of the pegs extending from the lattice (or ET plate) aid in the handling of tissues when transferring the lattice to new culture plates for medium changes, drug testing, or imaging purposes, among others. Without these pegs in place, it would e difficult to transfer the lattice without accidentally bumping the fragile tissues and potentially ruining the cultured cells. All of these advantages are apparent when read and viewed with disclosures and figures provided herein.

The various embodiments described herein provide methods and systems for implementing tissue growth in a high-throughput manner for both optical imaging-based and magnetic sensor-based contractility assays. In particular, the ET assemblies described herein, when used with the compatible casting plate described herein, provide significant advantages in cardiac and other ET contractility assays. Furthermore, the two-post, multi-well ET system assembly with flexible magnetic posts can be made compatible or be a part of a magnetic sensor-based contractile force measurement system disclosed in the U.S. Publication No. 2019/0029549 by Sniadecki.

Additionally, the various features of the present invention improve the manufacturability, reproducibility and utility of the consumable devices used for casting and generating the ET constructs and enables cost-effective, high-throughput measurements of the contractile forces of various ET constructs. Likewise, the various features of the stimulation plate and stimulation lid of the present invention provide advantages in electrically stimulating in a high-throughput manner the various types of cells or tissue constructs while improving the manufacturability, reproducibility, and utility of such consumable stimulation devices.

Furthermore, the stimulation lid in combination with the compatible ET assembly offers an advantageous means for monitoring or measuring contractile forces of the tissue constructs under simultaneous or non-simultaneous electrical stimulation.

Exemplary tissue constructs grown in the wells as described above may be engineered heart tissues (EHTs), which would have formed and been suspended between the two posts. These 3D cardiac tissues can generate from cardiomyocytes cast with the casting plate of the present disclosure and may be constructed with the two-post ET assembly of the present disclosure.

Figure 12:
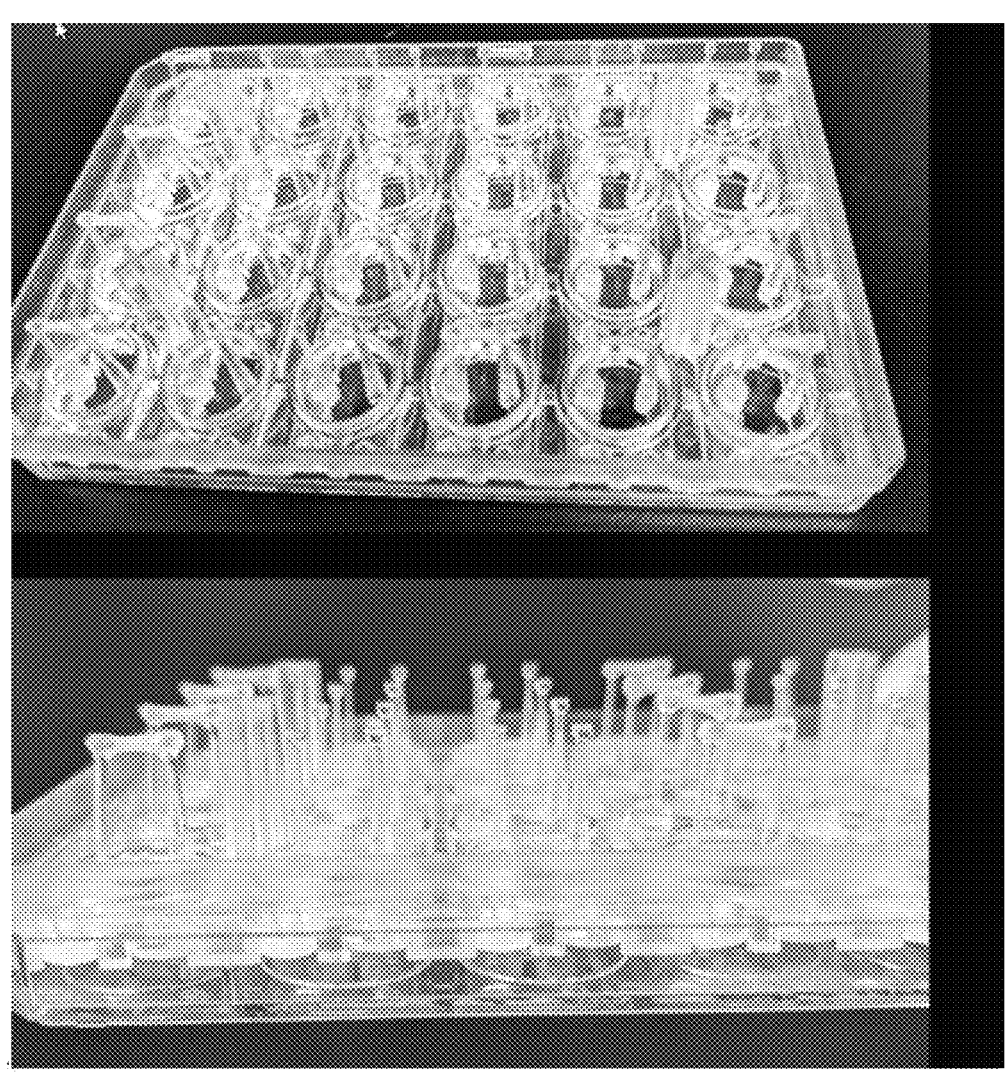
FIG. 12 shows views of the ET assembly with affixed tissues.
Figure 13:
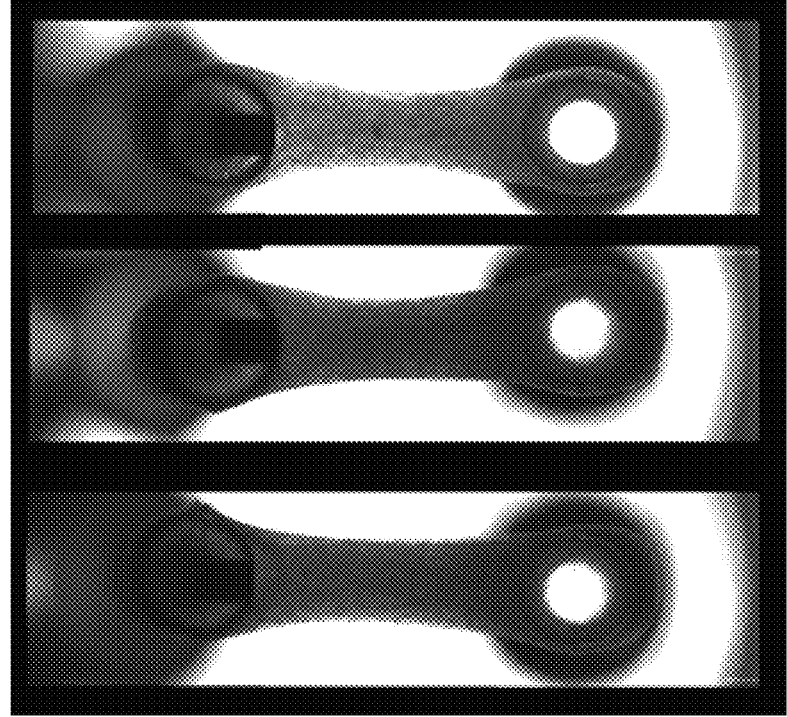
FIG. 13 shows magnified images of tissue affixed to two posts of flexible and rigid posts.

Exemplary 3D cardiac tissues were generated using the devices of the present disclosure from a WTC11 cell line of cardiomyocytes, as shown in FIGS. 12 and 13.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

This application claims the benefit of priority to U.S. Provisional Application No. 62/981,446, filed Feb. 25, 2020, which application is hereby incorporated by reference in its entirety.

The invention claimed is:

1. A casting assembly, comprising:
a casting plate comprising a plurality of casting wells, wherein each casting well of the plurality of casting wells includes a bottomless well arranged above a recessed well; and
an engineered tissue (ET) assembly, comprising:
an ET mounting lid comprising a plate comprising a first side, a second side, and a plurality of through holes;
a plurality of first posts; and
a plurality of second posts;
wherein the plurality of first posts and the plurality of second posts are arranged in pairs of posts, each pair of posts comprising a first post of the plurality of first posts and a second post of the plurality of second posts, wherein the pairs of posts are received in respective through holes of the plurality of through holes of the ET mounting lid and in respective casting wells of the plurality of casting wells of the casting plate, wherein ends of the pairs of posts are received in respective recessed wells.

2. The casting assembly of claim 1, wherein for each casting well, a size of the bottomless well is greater than a size of the recessed well.

3. The casting assembly of claim 1, wherein the recessed well is a tissue solution receptacle.

4. The casting assembly of claim 1, wherein for each casting well, a wall of the recessed well is sloped and a corner formed at the wall and a bottom surface of the recessed well is chamfered or curved.

5. The casting assembly of claim 1, wherein at least some of the first posts of the plurality of first posts are rigid posts and wherein at least some of the second posts of the plurality of second posts are flexible posts.

6. The casting assembly of claim 1, wherein at least some of the first posts of the plurality of first posts are flexible posts and wherein at least some of the second posts of the plurality of second posts are flexible posts.

7. The casting assembly of claim 1, wherein for each casting well of the plurality of casting wells, the bottomless well and the recessed well are formed as a single component.

8. The casting assembly of claim 1, wherein for each casting well of the plurality of casting wells, the bottomless well and the recessed well are formed as separate components.

9. The casting assembly of claim 1, wherein the casting plate comprises a first portion comprising the bottomless well of each casting well, and a second portion comprising the recessed well of each casting well.

10. The casting assembly of claim 9, wherein the first portion and the second portion are formed in a monolithic body.

11. The casting assembly of claim 1, wherein the plurality of first posts is arranged at a first side of the plurality of through holes and the plurality of second posts is arranged at a second side of the plurality of through holes.

12. The casting assembly of claim 1, wherein a first post assembly comprises at least some of the first posts of the plurality of first posts and wherein a second post assembly comprises at least some of the second posts of the plurality of second posts.

13. The casting assembly of claim 12, wherein the first post assembly is coupled to the ET mounting lid by first couplings, wherein the second post assembly is coupled to the ET mounting lid by second couplings.

14. The casting assembly of claim 1, wherein at least some of the second posts of the plurality of second posts are flexible posts.

15. The casting assembly of claim 14, wherein at least some of the flexible posts comprise a magnet.

16. The casting assembly of claim 15, wherein each of the magnets is disposed in a distal end of one of the flexible posts.

17. The casting assembly of claim 1, wherein for each of the casting wells, the bottomless well and the recessed well have a different shape in a plan view.

18. A system, comprising:
a tissue casting plate comprising a first portion having a plurality of bottomless wells and a second portion having a plurality of recessed wells, wherein the bottomless wells have a first shape and the recessed wells have a different second shape; and
an engineered tissue (ET) assembly, comprising:
an ET mounting lid comprising a plate comprising a first side, a second side, and a plurality of through holes;
a plurality of first posts; and
a plurality of second flexible posts;
wherein the plurality of first posts and the plurality of second flexible posts are arranged in pairs of posts, each pair of posts comprising a first post of the plurality of first posts and a second flexible post of the plurality of second flexible posts, wherein the pairs of posts are aligned with respective through holes of the plurality of through holes and wherein ends of the pairs of posts are received in respective recessed wells of the casting plate.

19. The system of claim 18, wherein the first portion and the second portion are formed as a monolithic body.

20. The system of claim 18, wherein at least some of the first posts of the plurality of first posts are rigid posts.

* * * * *